United States Patent
Grimmond et al.

(10) Patent No.: US 8,378,134 B2
(45) Date of Patent: *Feb. 19, 2013

(54) HYDROXYLATED CONTRAST ENHANCEMENT AGENTS

(75) Inventors: Brian James Grimmond, Clifton Park, NY (US); Michael Todd Luttrell, Clifton Park, NY (US); Jeannette Christine DePuy, Burnt Hills, NY (US); Mary Elizabeth Spilker, La Jolla, CA (US); Michael James Rishel, Saratoga Springs, NY (US)

(73) Assignee: General Electric Company, Niskayuna, NY (US)

( * ) Notice: Subject to any disclaimer, the term of this patent is extended or adjusted under 35 U.S.C. 154(b) by 350 days.

This patent is subject to a terminal disclaimer.

(21) Appl. No.: 12/570,705

(22) Filed: Sep. 30, 2009

(65) Prior Publication Data

US 2011/0076237 A1    Mar. 31, 2011

(51) Int. Cl.
*C07F 15/00* (2006.01)
*C07D 225/00* (2006.01)

(52) U.S. Cl. ........................ 556/148; 564/344

(58) Field of Classification Search ................... 556/148; 564/344

See application file for complete search history.

(56) References Cited

U.S. PATENT DOCUMENTS

| | | | |
|---|---|---|---|
| 3,632,637 A | 1/1972 | Martell | |
| 4,880,008 A | 11/1989 | Lauffer | |
| 4,899,755 A | 2/1990 | Lauffer et al. | |
| 4,909,257 A | 3/1990 | Engelstad et al. | |
| 4,957,939 A | 9/1990 | Gries et al. | |
| 5,227,474 A | 7/1993 | Johnson et al. | |
| 5,914,097 A * | 6/1999 | White | 424/9.365 |
| 6,531,510 B1 | 3/2003 | Bergeron, Jr. | |
| 6,646,157 B2 | 11/2003 | McKearin | |
| 7,081,472 B2 | 7/2006 | Cresens et al. | |
| 7,205,385 B2 | 4/2007 | Grimmond et al. | |
| 7,261,876 B2 | 8/2007 | Arbogast et al. | |
| 2004/0043030 A1 | 3/2004 | Griffiths et al. | |

FOREIGN PATENT DOCUMENTS

| | | |
|---|---|---|
| EP | 0230893 B1 | 6/1990 |
| EP | 0258616 B1 | 3/1992 |
| EP | 0222886 B1 | 9/1996 |
| WO | WO8606605 A1 | 11/1986 |
| WO | 9103200 A1 | 3/1991 |
| WO | 9833531 A1 | 8/1998 |
| WO | 2004064594 A2 | 8/2004 |
| WO | WO2007042506 A1 | 4/2007 |
| WO | WO2008085064 A2 | 8/2008 |
| WO | WO2009037235 A1 | 3/2009 |

OTHER PUBLICATIONS

PCT International Search Report dated Jan. 28, 2011 and Written Opinion.
Nicholas Richardson, Julian A. Davies, Bernd Raduchel; Iron(III)-based contrast agents for magnetic resonance imaging; Polyhedron Report No. 66; Polyhedron 18 (1999) 2457-2482.
Carla J. Mathias, Yizhen Sun, Michael J. Welch, Mark A. Green, Janice A. Thomas, Katrina R. Wade, and Arthur E. Martell; Targeting Radiopharmaceuticals: Comparative Biodistribution Studies of Gallium and Indium Complexes of Multidentate Ligands; Nucl. Med. Biol. vol. 15, No. I, pp. 69-81, 1988.

* cited by examiner

*Primary Examiner* — Andrew D Kosar
*Assistant Examiner* — Raymond Covington
(74) *Attorney, Agent, or Firm* — Andrew J. Caruso

(57) ABSTRACT

In one aspect, the present invention provides a contrast enhancement agent comprising an iron chelate having structure I

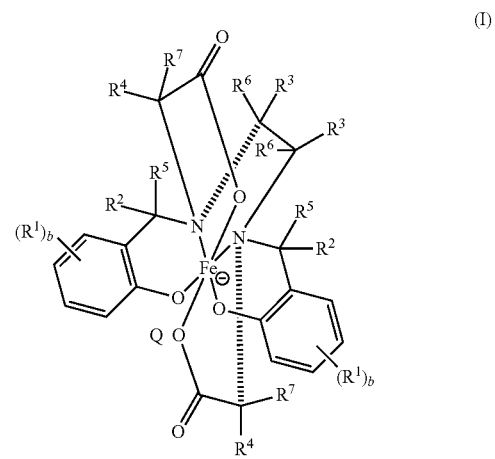

(I)

wherein $R^1$ is independently at each occurrence a hydroxy group, a $C_1$-$C_3$ hydroxyalkyl group, or a $C_1$-$C_3$ alkyl group, and b is 0-4; $R^2$-$R^7$ are independently at each occurrence hydrogen, a $C_1$-$C_3$ hydroxyalkyl group, or a $C_1$-$C_3$ alkyl group, with the proviso that at least one of $R^1$-$R^7$ is a hydroxy group or a $C_1$-$C_3$ hydroxyalkyl group; and wherein Q is a charge balancing counterion. Also provided is a metal chelating ligand having structure IX and medical formulations comprising the contrast enhancement I.

24 Claims, No Drawings

HYDROXYLATED CONTRAST ENHANCEMENT AGENTS

BACKGROUND

This invention relates to contrast enhancement agents for use in magnetic resonance imaging, more particularly to metal chelating ligands and metal chelate compounds useful in the preparation of such contrast enhancement agents.

Magnetic resonance (MR) imaging has become a critical medical diagnostic tool in human health. The use of MR contrast enhancement agents in MR imaging protocols has proven to be a valuable addition to the technique by improving both the quality of images obtained in an MR imaging procedure and the efficiency with which such images can be gathered. Known MR contrast enhancement agents suffer from a variety of deficiencies. For example, MR contrast enhancement agents containing gadolinium (Gd) chelates, while themselves are not toxic comprise gadolinium ion which in free ionic form is toxic. Contrast enhancement agents comprising chelates of manganese (Mn) may be subject to dissociation of the chelating ligand from the manganese metal center which is undesirable. Various other metal chelates may serve as MR contrast enhancement agents but are frequently less effective than gadolinium chelates and/or are not cleared from the body of the subject at sufficiently high rates following the imaging procedure.

Considerable effort and ingenuity has been expended to reduce the latent toxicity and control bio-distribution of MR contrast enhancement agents comprising gadolinium chelates. Potential MR contrast enhancement agents should exhibit good in-vivo and in-vitro stability, as well as prompt clearance from the body following an MR imaging procedure. MR contrast enhancement agents comprising a paramagnetic iron center are attractive because iron has an extensive and largely innocuous natural biochemistry as compared to gadolinium. This has led to increased interest in the use of iron-based materials as contrast agents for MR imaging.

There exists a need for additional iron-containing contrast enhancement agents for MR imaging that exhibit performance superior to or equivalent to known contrast enhancement agents while providing one or more additional advantages, such as improved image quality at lower patient dosages, greater patient tolerance and safety when higher doses are required, and improved clearance from the patient following the imaging procedure.

BRIEF DESCRIPTION

In one embodiment, the present invention provides a contrast enhancement agent comprising an iron chelate having structure I

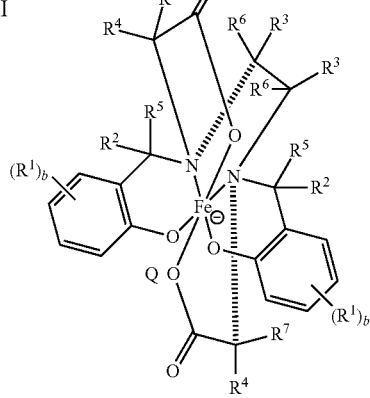

wherein $R^1$ is independently at each occurrence a hydroxy group, a $C_1$-$C_3$ hydroxyalkyl group, or a $C_1$-$C_3$ alkyl group, and b is 0-4; $R^2$-$R^7$ are independently at each occurrence hydrogen, a $C_1$-$C_3$ hydroxyalkyl group, or a $C_1$-$C_3$ alkyl group, with the proviso that at least one of $R^1$-$R^7$ is a hydroxy group or a $C_1$-$C_3$ hydroxyalkyl group; and wherein Q is a charge balancing counterion.

In another embodiment, the present invention provides a contrast enhancement agent having structure II

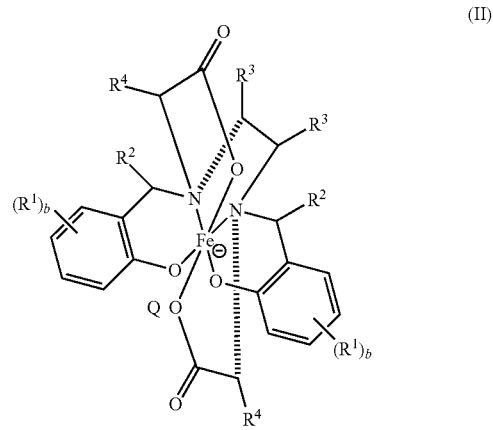

wherein $R^1$ is independently at each occurrence a hydroxy group, a $C_1$-$C_3$ hydroxyalkyl group, or a $C_1$-$C_3$ alkyl group, and b is 0-4; $R^2$-$R^4$ are hydrogen, a $C_1$-$C_3$ hydroxyalkyl group, or a $C_1$-$C_3$ alkyl group, with the proviso that at least one of $R^1$-$R^4$ is a hydroxy group or $C_1$-$C_3$ hydroxyalkyl group; and wherein Q is a charge balancing counterion.

In one embodiment, the present invention provides metal chelating ligand having idealized structure IX

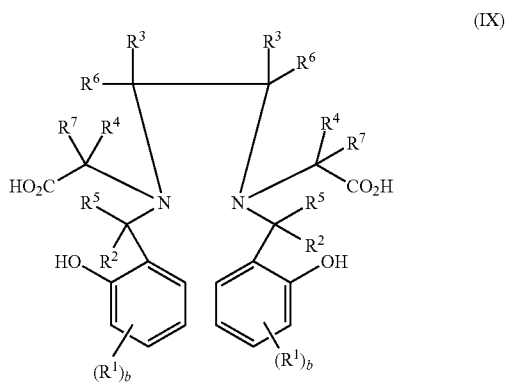

wherein $R^1$ is independently at each occurrence a hydroxy group, a $C_1$-$C_3$ hydroxyalkyl group, or a $C_1$-$C_3$ alkyl group, and b is 0-4; $R^2$-$R^7$ are independently at each occurrence hydrogen, a $C_1$-$C_3$ hydroxyalkyl group, or a $C_1$-$C_3$ alkyl group, with the proviso that at least one of $R^1$-$R^7$ is a hydroxy group or a $C_1$-$C_3$ hydroxyalkyl group.

In another embodiment, the present invention provides a metal chelating ligand having idealized structure X

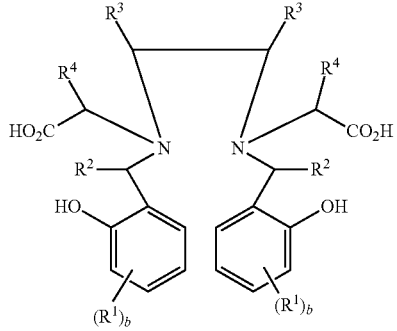

(X)

wherein $R^1$ is independently at each occurrence a hydroxy group, a $C_1$-$C_3$ hydroxyalkyl group, or a $C_1$-$C_3$ alkyl group, and b is 0-4; $R^2$-$R^4$ are hydrogen, a $C_1$-$C_3$ hydroxyalkyl group, or a $C_1$-$C_3$ alkyl group, with the proviso that at least one of $R^1$-$R^4$ is a hydroxy group or $C_1$-$C_3$ hydroxyalkyl group.

In yet another embodiment, the present invention provides a medical formulation comprising a contrast enhancement agent having structure I

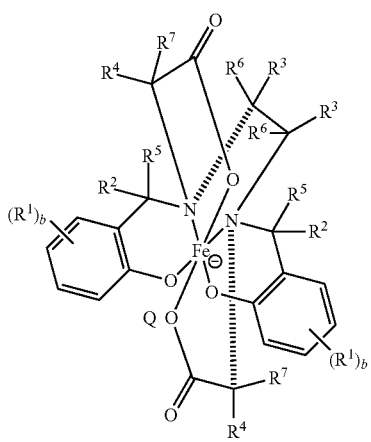

(I)

wherein $R^1$ is independently at each occurrence a hydroxy group, a $C_1$-$C_3$ hydroxyalkyl group, or a $C_1$-$C_3$ alkyl group, and b is 0-4; $R^2$-$R^7$ are independently at each occurrence hydrogen, a $C_1$-$C_3$ hydroxyalkyl group, or a $C_1$-$C_3$ alkyl group, with the proviso that at least one of $R^1$-$R^7$ is a hydroxy group or a $C_1$-$C_3$ hydroxyalkyl group; and wherein Q is a charge balancing counterion.

In yet another embodiment, the present invention provides a medical formulation comprising a contrast enhancement agent having structure II

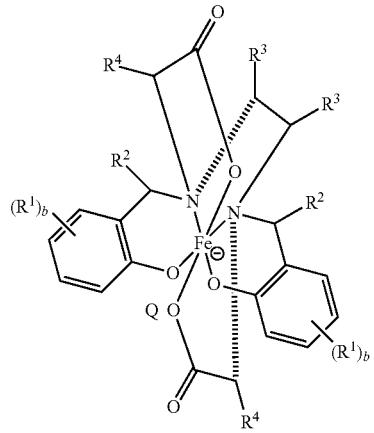

(II)

wherein $R^1$ is independently at each occurrence a hydroxy group, a $C_1$-$C_3$ hydroxyalkyl group, or a $C_1$-$C_3$ alkyl group, and b is 0-4; $R^2$-$R^4$ are hydrogen, a $C_1$-$C_3$ hydroxyalkyl group, or a $C_1$-$C_3$ alkyl group, with the proviso that at least one of $R^1$-$R^4$ is a hydroxy group or $C_1$-$C_3$ hydroxyalkyl group; and wherein Q is a charge balancing counterion.

DETAILED DESCRIPTION

In the following specification and the claims, which follow, reference will be made to a number of terms, which shall be defined to have the following meanings.

The singular forms "a", "an" and "the" include plural referents unless the context clearly dictates otherwise.

"Optional" or "optionally" means that the subsequently described event or circumstance may or may not occur, and that the description includes instances where the event occurs and instances where it does not.

As used herein, the term "solvent" can refer to a single solvent or a mixture of solvents.

Approximating language, as used herein throughout the specification and claims, may be applied to modify any quantitative representation that could permissibly vary without resulting in a change in the basic function to which it is related. Accordingly, a value modified by a term or terms, such as "about", is not to be limited to the precise value specified. In some instances, the approximating language may correspond to the precision of an instrument for measuring the value.

As noted in one embodiment, the present invention provides a contrast enhancement agent comprising an iron chelate having structure I

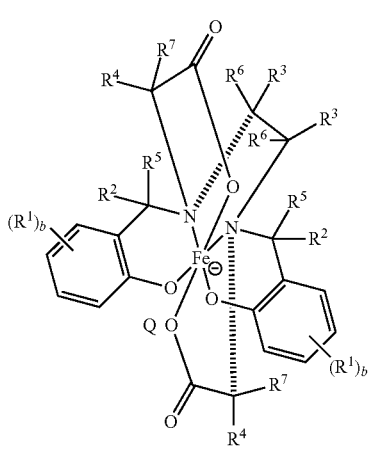

(I)

wherein $R^1$ is independently at each occurrence a hydroxy group, a $C_1$-$C_3$ hydroxyalkyl group, or a $C_1$-$C_3$ alkyl group, and b is 0-4; $R^2$-$R^7$ are independently at each occurrence hydrogen, a $C_1$-$C_3$ hydroxyalkyl group, or a $C_1$-$C_3$ alkyl group, with the proviso that at least one of $R^1$-$R^7$ is a hydroxy group or a $C_1$-$C_3$ hydroxyalkyl group; and wherein Q is a charge balancing counterion.

Although throughout this disclosure there is considerable focus on human health, the contrast enhancement agents provided by the present invention are useful in the study and treatment of variety of human and animal diseases as imaging agents, and as probes for the development of imaging agents.

Contrast enhancement agents comprising an iron chelate and falling within generic structure I are illustrated in Table 1 below

TABLE 1

Examples Of Iron Chelate Contrast Enhancement Agents Having Structure I

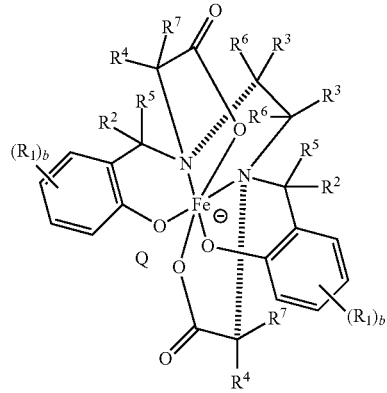

(I)

| Entry | Structure | Variables $R^1$-$R^7$ Defined As | Variable Q Defined As |
|---|---|---|---|
| 1a | 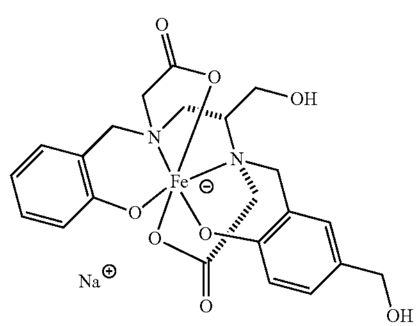 | $R^1$ is hydroxymethyl; $R^2$-$R^5$ are hydrogen; $R^6$ is hydroxymethyl and hydrogen; $R^7$ is hydrogen; b is 0 and 1. | $Na^+$ |

TABLE 1-continued

Examples Of Iron Chelate Contrast Enhancement Agents Having Structure I (I)

| Entry | Structure | Variables R¹-R⁷ Defined As | Variable Q Defined As |
|---|---|---|---|
| 1b | 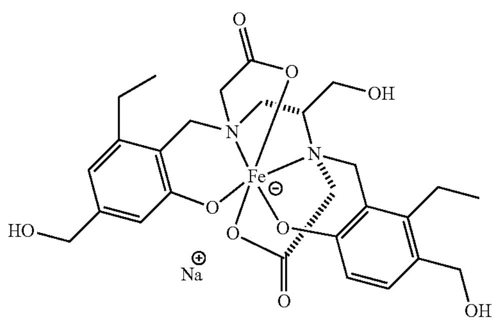 | $R^1$ is hydroxymethyl and ethyl; $R^2$-$R^5$ are hydrogen; $R^6$ is hydroxymethyl and hydrogen; $R^7$ is hydrogen; b is 2 | Na⁺ |
| 1c | 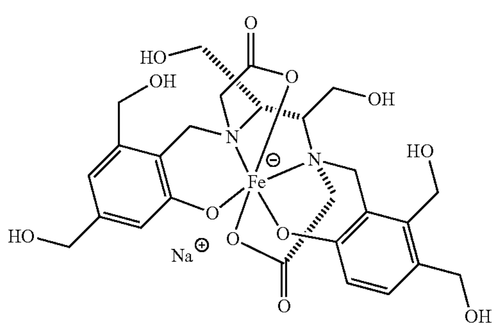 | $R^1$ is hydroxymethyl; $R^2$-$R^5$ are hydrogen, $R^6$ is hydroxymethyl; $R^7$ is hydrogen; b is 2 | Na⁺ |
| 1d | 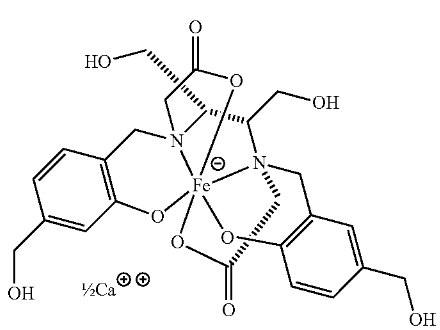 | $R^1$ is hydroxymethyl; $R^2$-$R^5$ are hydrogen; $R^6$ is hydroxymethyl; $R^7$ is hydrogen; b is 1. | ½ Ca⁺⁺ |

TABLE 1-continued

Examples Of Iron Chelate Contrast Enhancement Agents Having Structure I

| Entry | Structure | Variables R¹-R⁷ Defined As | Variable Q Defined As |
|---|---|---|---|
| 1e | 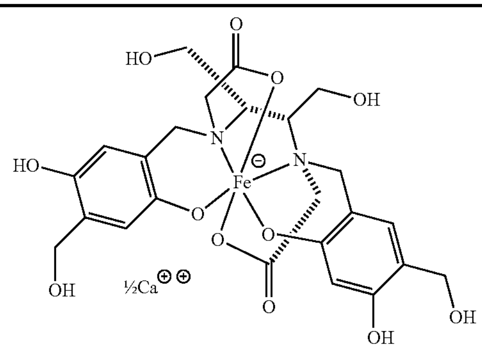 | $R^1$ is hydroxy and hydroxymethyl; $R^2$-$R^5$ are hydrogen; $R^6$ is hydroxymethyl; $R^7$ is hydrogen; b is 2. | ½ $Ca^{++}$ |

In general, and throughout this disclosure, no absolute or relative stereochemistry is intended to be shown for a structure, as in for example structures I and II, and the structures are intended to encompass all possible absolute and relative stereochemical configurations, unless specified otherwise. Thus, structure I depicts an iron chelate compound in which no absolute or relative stereochemistry is intended to be shown. As such, structure I is intended to represent a genus of iron chelate compounds which includes the racemic compounds, single enantiomers, enantiomerically enriched compositions and mixtures of diastereomers. In one embodiment, the present invention provides a contrast enhancement agent having structure 1a (Table 1) which is a racemic mixture having equal concentrations of levorotatory and dextrorotatory enantiomers of contrast enhancement agent 1a. In an alternate embodiment, the present invention provides a contrast enhancement agent having structure 1b (Table 1) which is an enantiomerically enriched mixture having unequal concentrations of levorotatory and dextrorotatory enantiomers of 1b. In yet another embodiment, the present invention provides a contrast enhancement agent having structure 1c (Table 1) which is a diastereomeric mixture comprising at least two compounds having structure 1c which are not enantiomers.

Those skilled in the art will appreciate that the iron chelate compositions provided by the present invention may comprise a principal component enantiomer, a minor component enantiomer, and additional diastereomeric iron chelate components. In one embodiment, the present invention provides an iron chelate composition comprising a principal component enantiomer and related diastereomers. In an alternate embodiment, the present invention provides an iron chelate composition having no principal component enantiomer and which is a diastereomeric mixture.

As noted, in another embodiment, the present invention provides a contrast enhancement agent comprising an iron chelate having structure II

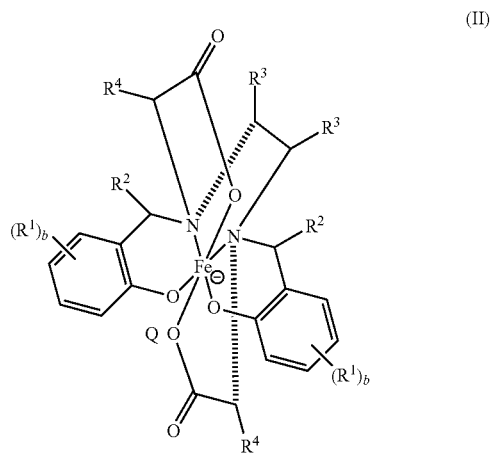

wherein $R^1$ is independently at each occurrence a hydroxy group, a $C_1$-$C_3$ hydroxyalkyl group, or a $C_1$-$C_3$ alkyl group and b is 0-4; $R^2$-$R^4$ are hydrogen, a $C_1$-$C_3$ hydroxyalkyl, group, or a $C_1$-$C_3$ alkyl group, with the proviso that at least one of $R^1$-$R^4$ is a hydroxy group or $C_1$-$C_3$ hydroxyalkyl group; and wherein Q is a charge balancing counterion.

Contrast enhancement agents comprising an iron chelate and falling within generic structure II are illustrated in Table 2 below.

TABLE 2

Examples Of Iron Chelate Contrast Enhancement Agents Having Structure II

| Entry | Structure | Variables $R^1$-$R^4$ Defined As | Variable Q Defined As |
|---|---|---|---|
| 2a | 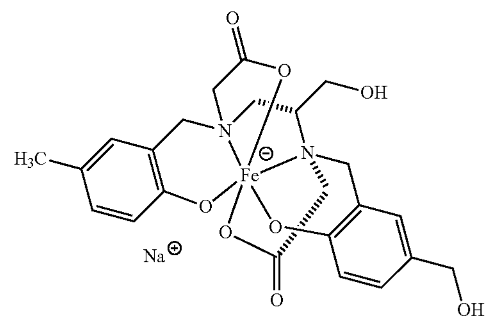 | $R^1$ is methyl, and hydroxymethyl; $R^2$ and $R^4$ are hydrogen; $R^3$ is hydroxymethyl and hydrogen; b is 1. | $Na^+$ |
| 2b | 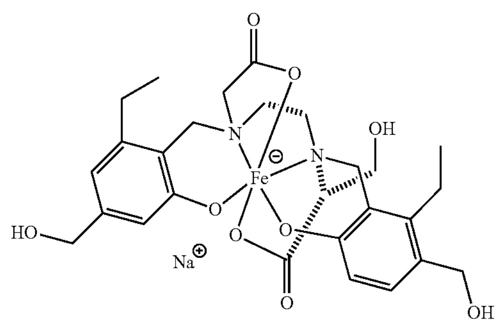 | $R^1$ is hydroxymethyl and ethyl; $R^2$-$R^3$ are hydrogen; $R^4$ is hydroxymethyl and hydrogen; b is 2. | $Na^+$ |
| 2c | 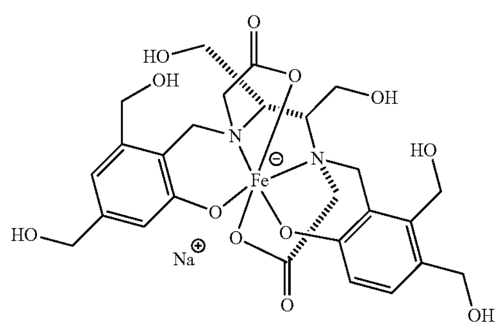 | $R^1$ is hydroxymethyl; $R^2$ and $R^4$ are hydrogen; $R^3$ is hydroxymethyl; b is 2. | $Na^+$ |
| 2d | 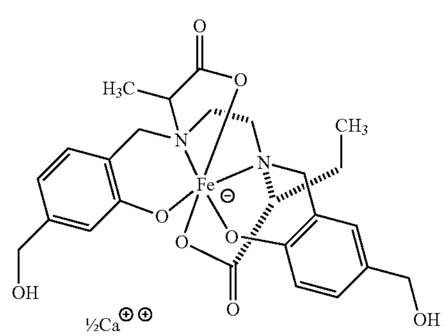 | $R^1$ is hydroxymethyl; $R^2$-$R^3$ are hydrogen; $R^4$ is methyl and ethyl; b is 1. | ½ $Ca^{++}$ |

TABLE 2-continued

Examples Of Iron Chelate Contrast Enhancement Agents Having Structure II

| Entry | Structure | Variables R¹-R⁴ Defined As | Variable Q Defined As |
|---|---|---|---|
| 2e | 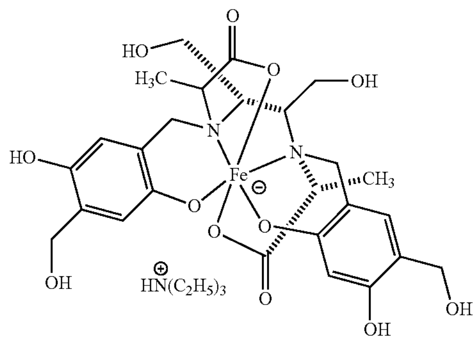 | $R^1$ is hydroxy and hydroxymethyl; $R^2$ is hydrogen; $R^3$ is hydroxymethyl; $R^4$ is methyl; b is 2. | $^+HN(C_2H_5)_3$ |

The charge balancing counterion Q may be an organic cation or an inorganic cation. Thus, in one embodiment, the charge balancing counterion Q is an inorganic cation. Non-limiting examples of inorganic cations include alkali metal cations, alkaline earth metal cations, transition metal cations, and inorganic ammonium cations ($NH_4^+$). In another embodiment, the charge balancing counterion Q is an organic cation, for example an organic ammonium cation, an organic phosphonium cation, an organic sulfonium cation, or a mixture thereof. In one embodiment, the charge balancing counterion is the ammonium salt of an aminosugar such as the 2-(N,N,N-trimethylammonium)-2-deoxyglucose. In one embodiment, the charge balancing counterion is the protonated form of N-methyl glucamine.

In one embodiment, the contrast enhancing agent includes an iron chelate having structure III

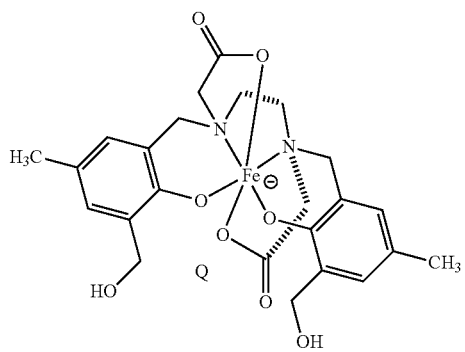

(III)

wherein Q is a charge balancing counterion.

In another embodiment, the contrast enhancing agent includes an iron chelate having structure IV

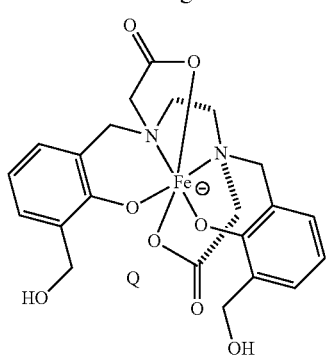

(IV)

wherein Q is a charge balancing counterion.

In another embodiment, the contrast enhancing agent includes an iron chelate having structure V

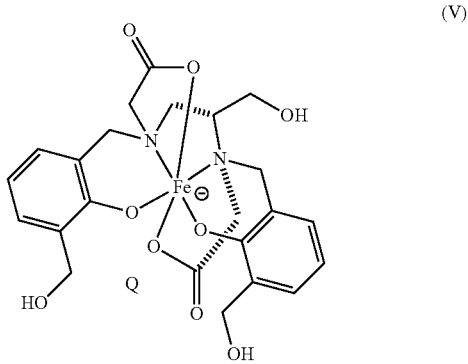

(V)

wherein Q is a charge balancing counterion.

In yet another embodiment, the contrast enhancing agent includes an iron chelate having structure VI

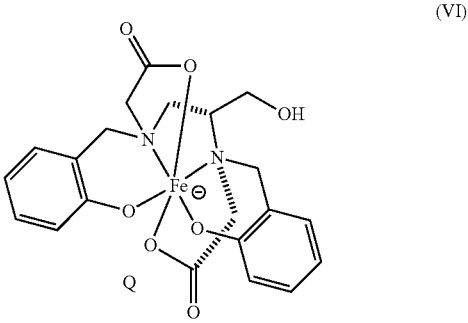

(VI)

wherein Q is a charge balancing counterion.

In another embodiment, the contrast enhancing agent includes an iron chelate having structure VII

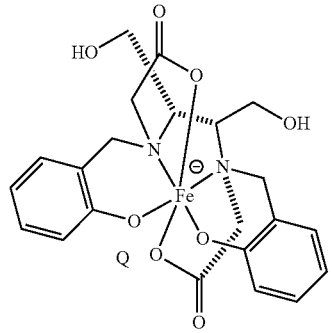

(VII)

wherein Q is a charge balancing counterion.

In yet another embodiment, the contrast enhancing agent includes an iron chelate having structure VIII

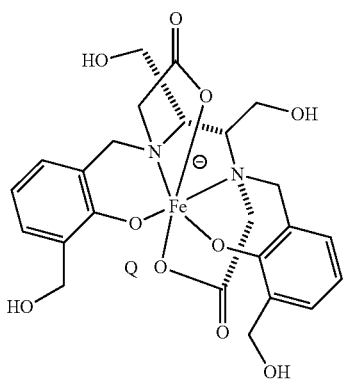

(VIII)

wherein Q is a charge balancing counterion.

In one embodiment, the present invention provides a metal chelating ligand having idealized structure IX

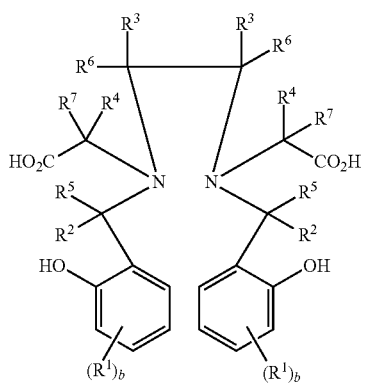

(IX)

wherein $R^1$ is independently at each occurrence a hydroxy group, a $C_1$-$C_3$ hydroxyalkyl group, or a $C_1$-$C_3$ alkyl group, and b is 0-4; $R^2$-$R^7$ are independently at each occurrence hydrogen, a $C_1$-$C_3$ hydroxyalkyl group, or a $C_1$-$C_3$ alkyl group, with the proviso that at least one of $R^1$-$R^7$ is a hydroxy group or a $C_1$-$C_3$ hydroxyalkyl group.

The term "idealized structure" is used herein to designate the structure indicated and additional structures which may include protonated and deprotonated forms of the metal chelating ligand having the idealized structure. Those having ordinary skill in the art will appreciate that the individual metal chelating ligands provided by the present invention may comprise protonated and deprotonated forms of the metal chelating ligand, for example the idealized structure of metal chelating ligand of structure IX comprises one or more of the protonated and the deprotonated forms having structure XVIII-XX.

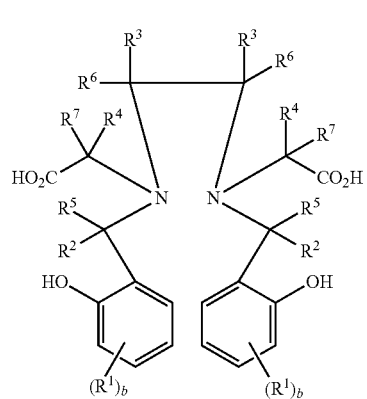

IX

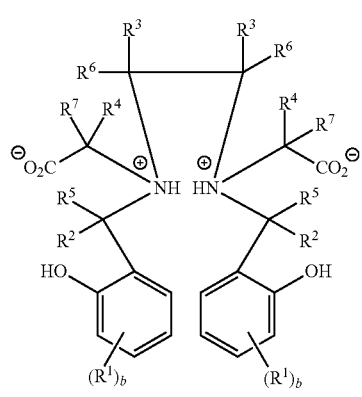

XVIII

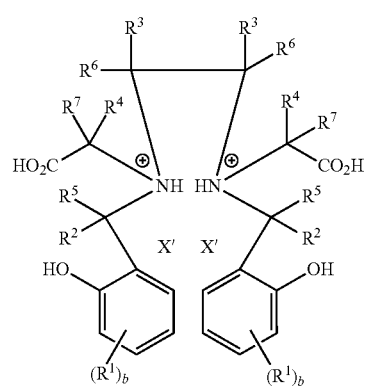

XIX

-continued

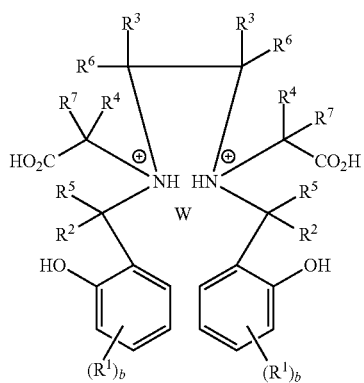

XX wherein W and X' are charge balancing counterions. In one embodiment, the charge balancing counterion X' may be an inorganic anion or an organic anion. Similarly, W may be an inorganic anion or an organic anion. Thus, in one embodiment, the charge balancing counterion W is an inorganic anion. In another embodiment, the charge balancing counterion W is an organic anion. Similarly, in one embodiment, the charge balancing counterion X' is an inorganic anion. In another embodiment, the charge balancing counterion X' is an organic anion. Those skilled in the art will appreciate that charge balancing counterions X' include monovalent anions such as chloride, bromide, iodide, bicarbonate, acetate, glycinate, ammonium succinate, and the like. Similarly, those skilled in the art will appreciate that charge balancing counterions W include polyvalent anions such as carbonate, sulfate, succinate, malonate, and the like.

Metal chelating ligands having idealized structure IX are further illustrated in Table 3 below.

TABLE 3

Examples Of Metal Chelating Ligands Having Structure IX

| Entry | Structure | Variables $R^1$-$R^7$ Defined As | W | X' |
|---|---|---|---|---|
| 3a | 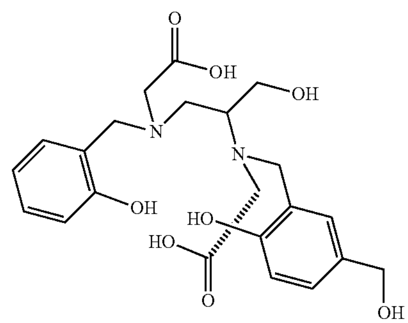 | $R^1$ is hydroxymethyl; $R^2$-$R^5$ are hydrogen; $R^6$ is hydroxymethyl and hydrogen; $R^7$ is hydrogen; b is 0 and 1. | — | — |
| 3b | 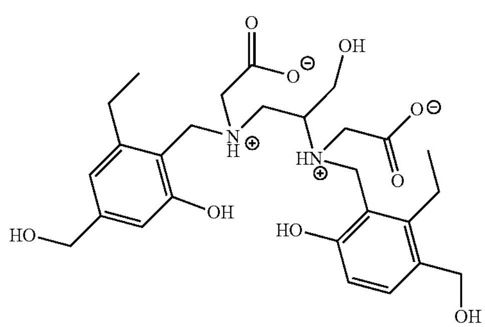 [SMILES: CCc1cc(CO)cc(O)c1C[NH+](CC(=O)[O-])CC(CO)[NH+](CC(=O)[O-])Cc1c(O)ccc(CO)c1CC] | $R^1$ is hydroxymethyl and ethyl; $R^2$-$R^5$ are hydrogen; $R^6$ is hydroxymethyl and hydrogen; $R^7$ is hydrogen; b is 2. | — | — |
| 3c | 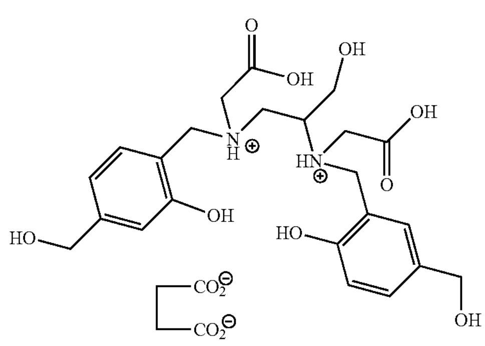 | $R^1$ is hydroxymethyl; $R^2$-$R^5$ are hydrogen; $R^6$ is hydroxymethyl and hydrogen; $R^7$ is hydrogen; b is 1. | $\begin{array}{c}-CO_2^\ominus\\-CO_2^\ominus\end{array}$ (succinate) | — |

TABLE 3-continued

Examples Of Metal Chelating Ligands Having Structure IX

| Entry | Structure | Variables $R^1$-$R^7$ Defined As | W | X' |
|---|---|---|---|---|
| 3d | 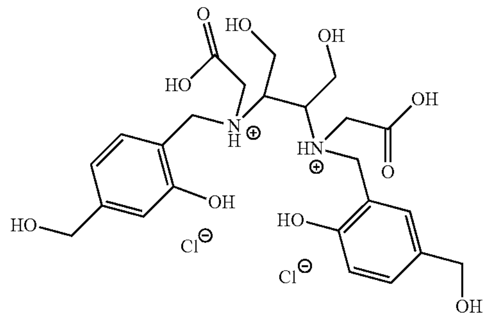 [SMILES: O=C(O)C[NH+](Cc1ccc(CO)cc1O)C(CO)C(CO)[NH+](CC(=O)O)Cc1cc(CO)ccc1O ; [Cl-] ; [Cl-]] | $R^1$ is hydroxymethyl; $R^2$-$R^5$ are hydrogen; $R^6$ is hydroxymethyl; $R^7$ is hydrogen; b is 1. | — | Cl⁻ |

In an alternate embodiment, the present invention provides a metal chelating ligand having an idealized structure X

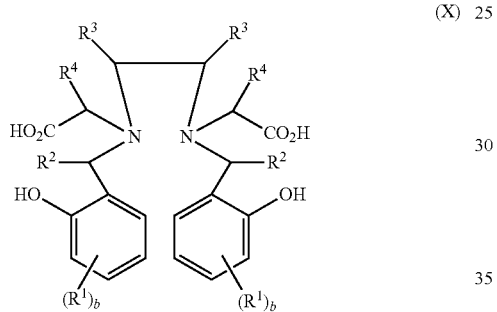
(X)

wherein $R^1$ is independently at each occurrence a hydroxy group, a $C_1$-$C_3$ hydroxyalkyl group, or a $C_1$-$C_3$ alkyl group, and b is 0-4; $R^2$-$R^4$ are hydrogen, a $C_1$-$C_3$ hydroxyalkyl group, or a $C_1$-$C_3$ alkyl group, with the proviso that at least one of $R^1$-$R^4$ is a hydroxy group or $C_1$-$C_3$ hydroxyalkyl group.

The metal chelating ligands having structure X are illustrated in Table 4 below.

TABLE 4

Examples Of Metal Chelating Ligands Having Structure X

| Entry | Structure | Variables $R^1$-$R^4$ Defined As | W | X' |
|---|---|---|---|---|
| 4a | 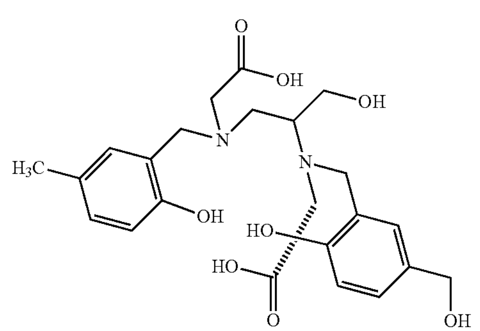 | $R^1$ is methyl and hydroxymethyl; $R^2$ and $R^4$ are hydrogen; $R^3$ is hydroxymethyl and hydrogen; b is 1. | — | — |

TABLE 4-continued

Examples Of Metal Chelating Ligands Having Structure X

| Entry | Structure | Variables $R^1$-$R^4$ Defined As | W | X' |
|---|---|---|---|---|
| 4b | 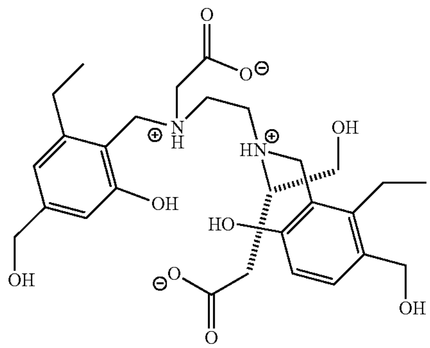 [SMILES: CCc1cc(CO)cc(O)c1C[NH+](CC[NH+](Cc1c(O)ccc(CO)c1CC)[C@H](CO)CC(=O)[O-])CC(=O)[O-]] | $R^1$ is hydroxymethyl and ethyl; $R^2$-$R^3$ are hydrogen; $R^4$ is hydroxymethyl and hydrogen; b is 2. | — | — |
| 4c | 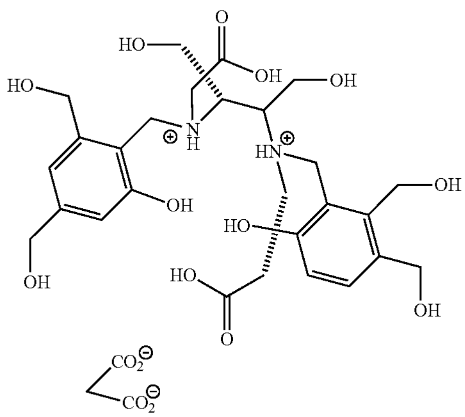 | $R^1$ is hydroxymethyl; $R^2$ and $R^4$ are hydrogen; $R^3$ is hydroxymethyl; b is 2. | (malonate) | |
| 4d | 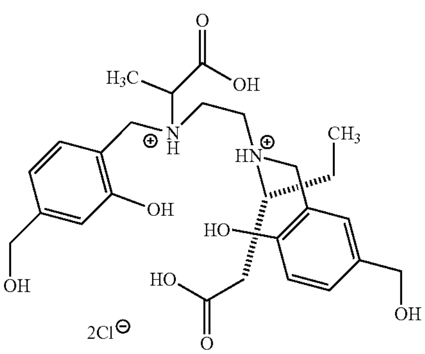 [SMILES: CC[C@H](CC(=O)O)[NH+](CC[NH+](Cc1ccc(CO)cc1O)C(C)C(=O)O)Cc1cc(CO)ccc1O] | $R^1$ is hydroxymethyl; $R^2$-$R^3$ are hydrogen; $R^4$ is methyl and ethyl; b is 1. | — | Cl$^-$ |
| 4e | 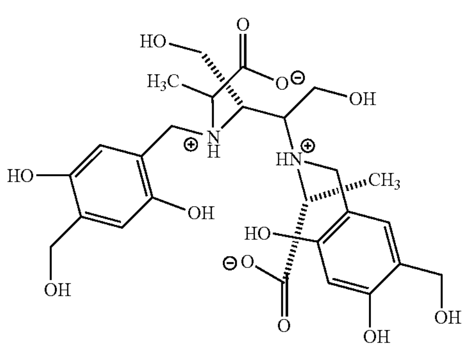 | $R^1$ is hydroxy and hydroxymethyl; $R^2$ is hydrogen $R^3$ is hydroxymethyl; $R^4$ is methyl; b is 2. | — | — |

The metal chelating ligands form coordinate complexes with a variety of metals. In one embodiment, the metal chelating ligands form complexes with transition metals. In a particular embodiment, the transition metal is iron.

In one embodiment, the metal chelating ligand has an idealized structure XI.

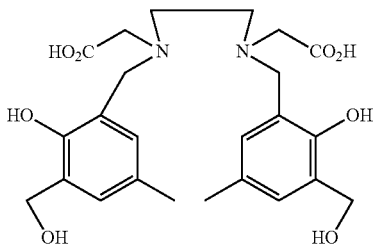
(XI)

In another embodiment, the metal chelating ligand has an idealized structure XII.

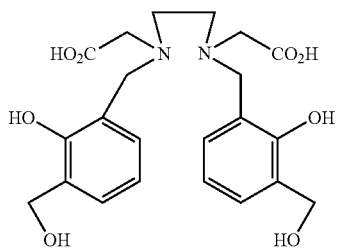
(XII)

In yet another embodiment, the metal chelating ligand has an idealized structure XIII.

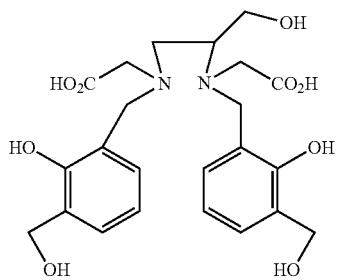
(XIII)

In another embodiment, the metal chelating ligand has an idealized structure XIV.

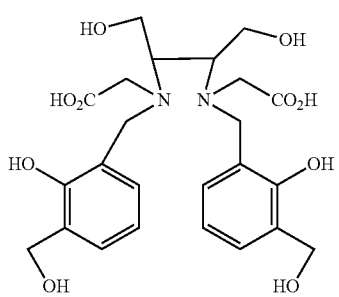
(XIV)

In one embodiment, the present invention provides a medical formulation comprising the contrast enhancement agent having structure I. In yet another embodiment, the present invention provides a medical formulation comprising the contrast enhancement agent having structure II. In another embodiment, the medical formulations provided by the present invention comprise at least one structure selected from structures III, IV, V, VI, VII and VIII. The contrast enhancement agents provided by the present invention are suitable for use as imaging agents for magnetic resonance (MR) screening of human patients for various pathological conditions. As will be appreciated by those of ordinary skill in the art, MR imaging has become a medical imaging technique of critical importance to human health. In one embodiment, the present invention provides a method for increasing the emitted signal, and thus obtaining in vivo differentiation of tissues in an organism by administering a contrast enhancement agent of the present invention to a living subject and conducting magnetic resonance imaging of the subject. In one embodiment, the contrast enhancement agent provided by the present invention includes an iron chelate wherein the iron is paramagnetic. Contrast enhancement agents provided by the present invention comprising a paramagnetic iron center are believed to be more readily excreted by human patients and by animals and as such are more rapidly and completely cleared from the patient following the magnetic resonance imaging procedure. In addition, the contrast enhancement agents provided by the present invention may enable the administration of lower levels of the contrast enhancement agent to the patient relative to know contrast enhancement agents without sacrificing image quality. Thus, in one embodiment, useful MR contrast enhancement using the contrast enhancement agent of the present invention is achieved at lower dosage level in comparison with known MR contrast agents. In an alternate embodiment, the contrast enhancement agents provided by the present invention may administered to a patient at a higher dosage level in comparison with known MR contrast agents in order to achieve a particular result. Higher dosages of the contrast enhancement agents of the present invention may be acceptable in part because of the enhanced safety of such iron based contrast enhancement agents, and improved clearance of the contrast enhancement agent from the patient following the imaging procedure. In one embodiment, contrast enhancement agent is administered in a dosage amount corresponding to from about 0.001 to about 5 millimoles per kilogram weight of the patient. As will be appreciated by those of ordinary skill in the art, contrast enhancement agents provided by the present invention may be selected and/or further modified to optimize the residence time of the contrast enhancement agent in the patient, depending on the length of the imaging time required.

In one embodiment, the contrast enhancement agent according to the present invention may be used for imaging the circulatory system, the genitourinary system, hepatobiliary system, central nervous system, for imaging tumors, abscesses and the like. In another embodiment, the contrast enhancement agent of the present invention may also be useful to improve lesion detectability by MR enhancement of either the lesion or adjacent normal structures.

The contrast enhancement agent may be administered by any suitable method for introducing a contrast enhancement agent to the tissue area of interest. The medical formulation containing the contrast enhancement agent is desirably sterile and is typically administered intravenously and may contain various pharmaceutically acceptable agents, which promote the dispersal of the MR imaging agent. In one embodiment, the medical formulation provided by the present invention is an aqueous solution. In one embodiment, the MR imagining agent may be administered to a patient in an aqueous formulation comprising ethanol and the contrast enhancement agent. In an alternate embodiment, the MR imagining agent may be administered to a patient as an aqueous formulation comprising dextrose and the contrast enhancement agent. In yet another embodiment, the MR imagining agent may be administered to a patient as an aqueous formulation comprising saline and the contrast enhancement agent.

In addition to being useful as MR imaging agents and as probes for determining the suitability of a given iron chelate compound for use as a MR imaging agent, the contrast enhancement agents provided by the present invention may also, in certain embodiments, possess therapeutic utility in the treatment of one or more pathological conditions in humans and/or animals. Thus, in one embodiment, the present invention provides a contrast enhancement agent having structure I, which is useful in treating a pathological condition in a patient. In an alternate embodiment, the present invention provides a contrast enhancement agent having structure II, which is useful in treating a pathological condition in a patient.

Those skilled in the art will appreciate that iron chelate compounds falling within the scope of generic structure I may under a variety of conditions form salts which are useful as MR imaging agents, probes for the discovery and development of imaging agents, and/or as therapeutic agents. Thus, the present invention provides a host of novel and useful iron chelate compounds and their salts.

The contrast enhancement agent of the present invention may be prepared by a variety of methods including those provided in the experimental section of this disclosure. For example, stoichiometric amounts of the metal ion and the metal chelating ligand may be admixed in a solution with an appropriate adjustment of pH, if necessary. The contrast enhancement agent may be isolated by conventional methods such as crystallization, chromatography, and the like, and admixed with conventional pharmaceutical carriers suitable for pharmaceutical administration.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

EXAMPLES

Method 1 Preparation of Diamine Compound 1

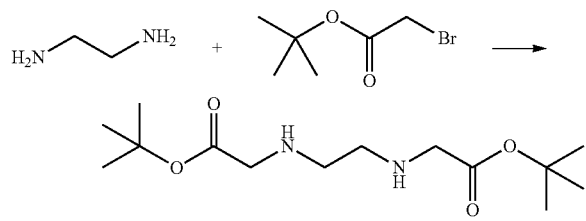

A solution of tert-butylbromoacetate (3.41 g, 17.47 mmol) in 5 milliliter (mL) dimethyl formamide (DMF) was added to a solution of ethylene diamine (1.05 g, 17.47 mmol) in anhydrous dimethylformamide (30 mL) at 0° C. via a syringe pump. The addition of the tert-butylbromoacetate solution was carried out for a period of about 30 min. The reaction mixture was allowed to stand for about 2 h. At the end of the stipulated time the reaction mixture was analyzed by liquid chromatography mass spectrometry (LC-MS). The LC-MS analysis indicated the presence of a statistical mixture of alkylated products including mono, bis, bis', tri, and tetrasubstituted products. The reaction mixture was then concentrated under reduced pressure and purified by C-18 reversed phase chromatography. The collected fractions containing the diamine compound 1, were combined and were evaluated by LC-MS, m/z=289 [M+H]+.

Method 2 Preparation of Aldehyde Compound 2

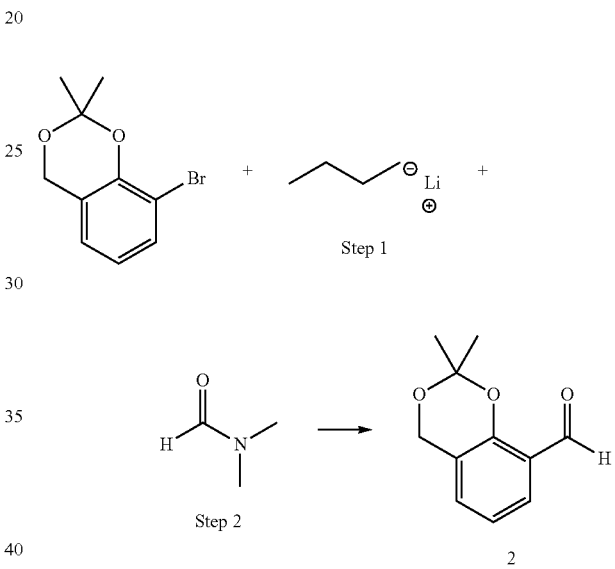

3-bromosalicyl alcohol isopropylidene acetal (5.05 g, 22.1 mmol) was prepared as using the method described in Meier C. et al. *Eur J. Org. Chem.* 2006, 197. About 8.31 mL of n-BuLi in hexanes (20.77 mmol) was diluted with 30 mL of anhydrous tetrahydrofuran (THF). The diluted n-BuLi was cooled to a temperature of about −75° C. A solution of 3-bromosalicyl alcohol isopropylidene acetal in about 15 mL anhydrous THF was then added over a period of 1.5 h, while maintaining the internal reaction temperature at or below −70° C. in an acetone/dry ice bath. Following the addition of the 3-bromosalicyl alcohol isopropylidene acetal, the reaction mixture was stirred for an additional 30 min while maintaining the temperature at or below −70° C. At the end of 30 min anhydrous DMF (1.62 mL, 20.77 mmol) was added to the reaction mixture over a period of 30 sec. The reaction mixture was allowed to re-equilibrate to a temperature of about −70° C., and the reaction mixture warmed to about 0° C. The reaction mixture was then quenched by the addition of methanol (30 mL), and was poured into saturated aqueous NaHCO$_3$, and then extracted with dichloromethane (3×75 mL). The combined organic extracts were dried over MgSO$_4$, filtered, and concentrated under reduced pressure to provide a yellow oil that solidified on standing under high vacuum. The crude material was purified by flash chromatography (SiO$_2$, 40 g column, isocratic, 10% EtOac-hexanes, 254 and 327 nm) to afford the aldehyde compound, 2, as a pale yellow solid, m/z=195 [M+3H]+.

Method 3 Preparation of Compound 3

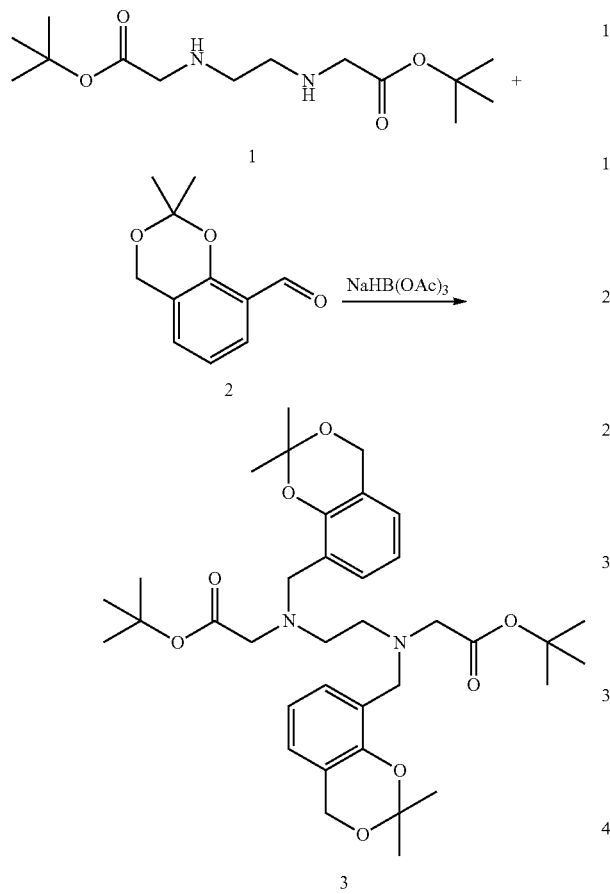

The diamine compound 1 (0.1 g, 0.35 mmol) and the aldehyde compound 2 (0.13 g, 0.69 mmol) were dissolved in 1,2 dichloroethane (3.5 mL) followed by the addition of sodium acetoxyborohydride (0.33 g, 1.56 mmol) under stirring. The reaction mixture was allowed to stirring at room temperature overnight. Following the allotted time, the reactions progress was monitored by LC-MS. The reaction mixture was then quenched by the addition of saturated sodium bicarbonate solution and diluted with dichloromethane (10 mL). The aqueous and organic layers were separated and the aqueous layer was extracted with dichloromethane (3×25 mL). The combined organic layers were washed with saturated aqueous solutions of sodium bicarbonate, (2×25 mL), brine (2×25 mL) and dried over $MgSO_4$. The solution was filtered and concentrated under reduced pressure to provide the crude product as a pale yellow oil. The crude product was purified by flash chromatography ($SiO_2$, 12 g) using the following gradient program at 30 mL/min: 100% hexanes for 3 column volumes, then ramp to 35% EtOAc-hexanes over 20 column volumes, finally holding at 35% EtOAc-hexanes for 5 column volumes. The column eluant was monitored at 289 nm and the purified compound was pooled and concentrated under reduced pressure. The compound 3, was a colorless oil that was further dried under high vacuum, m/z=642 [M+H]+.

Example 1

Preparation of Ligand XII

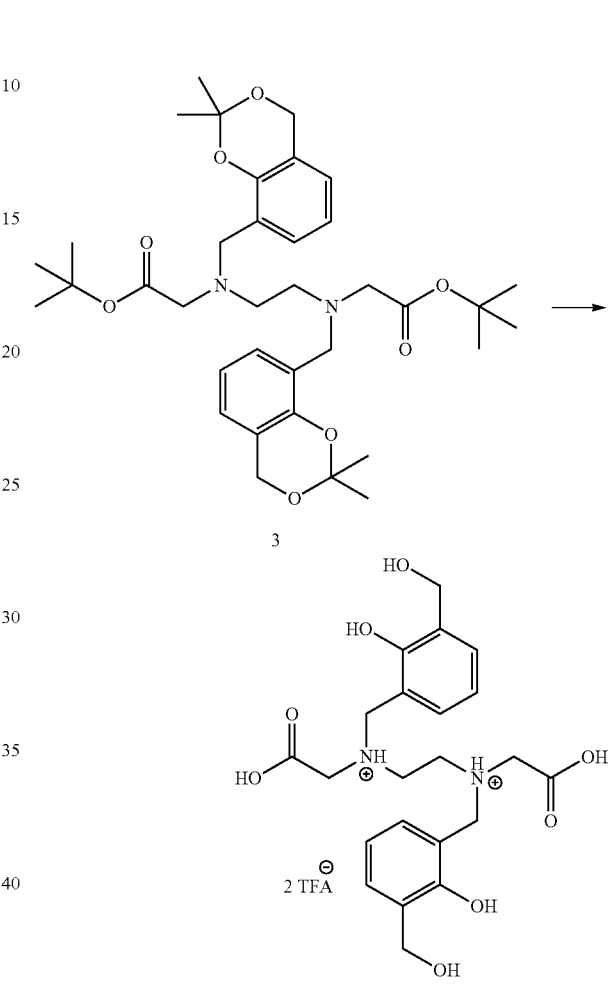

A mixture of dioxane (0.71 mL) and water (0.36 mL) were added to about 0.11 g of compound 3 (0.18 mmol) followed by the addition of 4M HCl in dioxane (0.71 mL). The reaction mixture was heated to a temperature of about 72° C. for about 2 h. Analysis on the reaction mixture was carried out by LC-MS to ensure completion of the reaction. The reaction mixture was neutralized using a stoichiometric amount of 4M NaOH and the final pH of the reaction mixture was about 6. The excess solvent was removed under reduced pressure to provide a yellow foam that was analyzed by LC-MS to contain the crude ligand XII, with quantities of decomposition products. The reaction mixture was purified by preparative high performance liquid chromatography (HPLC) on C18 functionalized silica gel (10×100 mm waters xTerra Prep C18 5 um) using the following gradient program at 9 mL/min: 2% MeCN-water containing 0.05% TFA for 0.5 minutes, then ramp to 60% MeCN-water containing 0.05% TFA over 14.5 minutes, finally holding at 60% MeCN-water containing 0.05% TFA for 3 minutes. The column eluant was monitored at 285 nm and the fractions containing the purified material were pooled and concentrated under reduced pressure to provide the ligand XII, as a colorless oil, m/z=449 [M+H]+.

Example 2

Preparation of FeHBED(OH)$_2$ IV

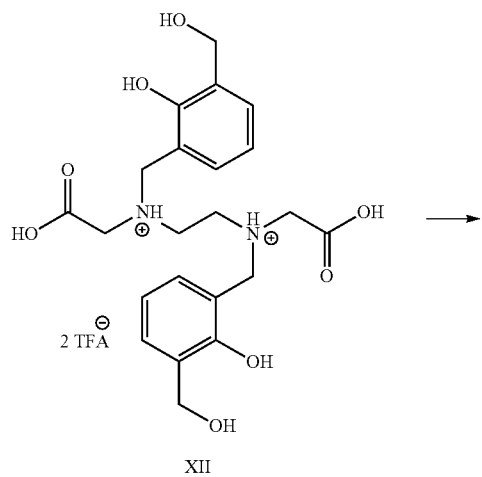

An aliquot of distilled water (1.0 mL) was added to about 4.5 mg of ligand XII (7.0 mmol) resulting in the formation of a clear solution. About 1.5 mg of FeCl$_3$.6H$_2$O (6 mmol) dissolved in distilled water (100 mL) was added immediately to the ligand solution to form a dark red solution that was then quenched with NaHCO$_3$ (300 uL, 0.1M). The reaction mixture was passed through a Sephadex G-10 column, eluting with distilled water to afford the compound FeHBED(OH)$_2$ IV wherein Q is a sodium cation as a clear red solution, m/z=501 [M+H]+, 524 [M+Na]+.

Method 4 Preparation of Aldehyde Compound 4

The aldehyde compound 4 was prepared according to a procedure given in Koskinen, A. M. P.; Abe, A. M. M.; Helaja, J. *Org. Lett.* 2006, 8, 20, 4537 incorporated herein.

Method 5 Preparation of Compound 5

About 0.1 g of the diamine compound 1, (0.35 mmol) and about 0.14 g aldehyde compound 6 (0.69 mmol) were dissolved in 1,2 dichloroethane (3.5 mL) followed by the addition of sodium acetoxyborohydride (0.33 g, 1.56 mmol). The reaction mixture was stirred at room temperature overnight and completion of the reaction was confirmed by LC-MS. The reaction mixture was the quenched by the addition of saturated sodium bicarbonate solution and diluted with dichloromethane (10 mL). The aqueous and organic layers were separated and the aqueous layer was extracted with dichloromethane (3×25 mL). The combined organic layers were washed with saturated aqueous sodium bicarbonate solution, (2×25 mL), brine (2×25 mL) and dried over $MgSO_4$. The solution was then filtered and concentrated under reduced pressure to provide the crude product as a pale yellow oil. The crude product was purified by flash chromatography ($SiO_2$, 12 g) using the following gradient program at 30 mL/min: 100% hexanes for 3 column volumes, then ramp to 35% EtOAc-hexanes over 20 column volumes, finally holding at 35% EtOAc-hexanes for 5 column volumes. The column eluant was monitored at 289 nm and fractions containing the purified material were pooled and concentrated under reduced pressure to yield the compound 5, as a colorless oil, m/z=669 [M+H]+.

-continued

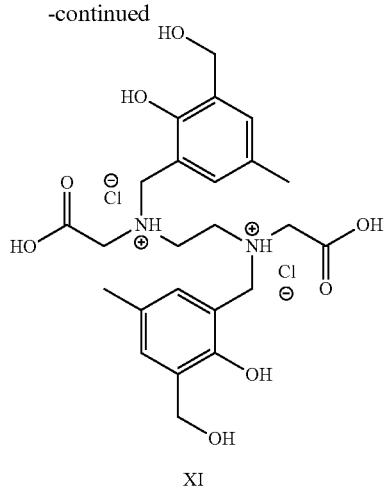

XI

Dioxane (0.88 mL) and water (0.44 mL) were added to about 0.15 g of the compound 5 (0.22 mmol), followed by the addition of about 4M HCl in dioxane (0.88 mL). The reaction mixture was allowed to stir at room temperature overnight and then heated for about 90 min at a temperature of about 72° C. At the end of the allotted time the completion of the reaction was confirmed by LC-MS. The reaction mixture was then concentrated under reduced pressure and further dried under high vacuum to provide ligand XI as a white solid, m/z=477 [M+H]+. It should be noted that a small degree of decomposition (~5-10%) was noted on concentration of the product mixture.

Example 3

Preparation of Ligand XI

Example 4

Preparation of FeHBED(Me)$_2$(OH)$_2$ III

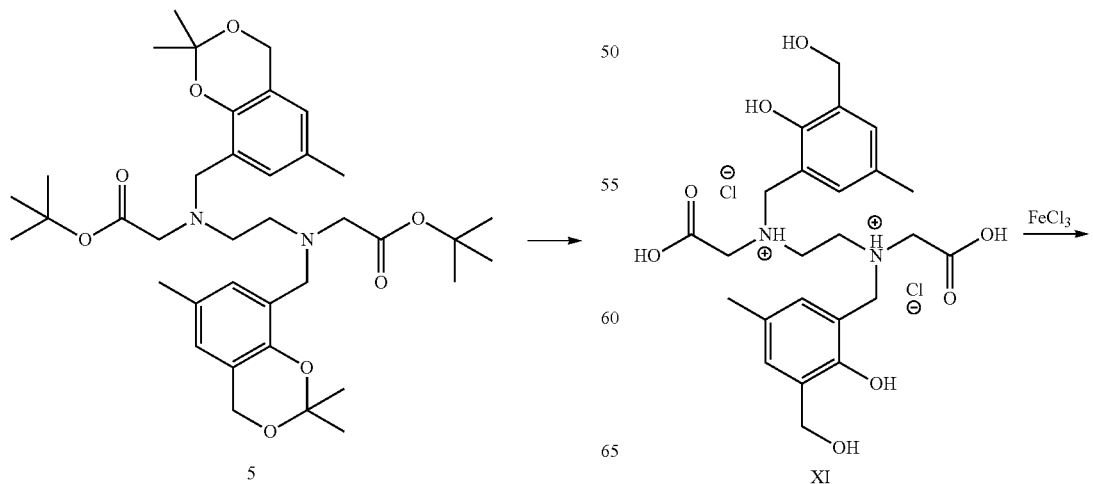

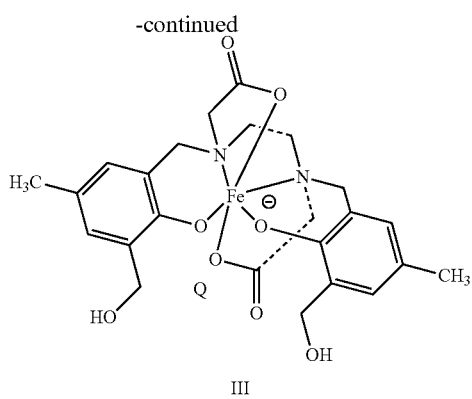

III

An aliquot of distilled water (1.5 mL) was added to about 5.0 mg of ligand XI (10 mmol) and $FeCl_3 \cdot 6H_2O$ (2.2 mg, 8.1 mmol) to form a cloudy purple solution. An aliquot of $NEt_3HCO_3$ (0.5 mL, 0.1 M) was added to neutralize the reaction mixture, resulting in the formation of a clear dark purple solution containing crude III, as confirmed by LC-MS, which was stirred for 12 h. The reaction mixture was passed through a Sephadex G-10 plug, eluting with deionized water followed by a wash with diethyl ether (2×2 mL) to afford a purple solution from which the volatiles were removed. The resulting purple solid was washed with $CH_3CN$ (2×1 mL) and dried in-vacuo to give compound III, wherein the charge balancing counterion Q is triethylammonium, as a purple solid, m/z=530 [M+2H]+.

Method 6 Preparation of Diamine Compound 6

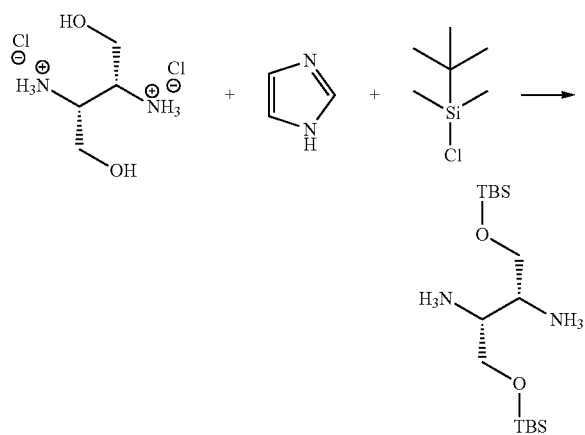

To a solution of 2,3-diamino butane-1,4-diol bishydrochloride having the absolute stereochemistry shown (1.0 g, 5.8 mmol) in dichloromethane (52 mL) imidiazole (1.7 g, 25.9 mmol) was added followed by addition of t-butyldimethylsilyl chloride (TBDMS-Cl) (1.6 g, 10.6 mmol). The reaction mixture was allowed to stir overnight, and then quenched by the addition of saturated aqueous potassium carbonate solution. The aqueous and organic layers were separated. The aqueous layer was extracted with dichloromethane (3×25 mL) and the combined organic layers were washed with saturated aqueous potassium carbonate solution, (2×25 mL), brine and dried over $MgSO_4$. The solution was filtered and concentrated under reduced pressure to provide the crude product 6 as a crystalline solid. The crude product 6 was purified by flash chromatography on normal phase silica gel (40 gram column) using the following gradient program at 40 mL/min: 100% dichloromethane w/0.5% triethylamine for 2 column volumes, then ramp to 20% MeOH-Dichloromethane each w/0.5% triethylamine over 20 column volumes, finally holding at 20% MeOH-Dichloromethane each w/0.5% triethylamine for 3 column volumes. The column eluant was monitored at 230 nm and the fractions containing the purified diamine compound 6 were pooled and concentrated under reduced pressure. Drying in-vacuo afforded diamine compound 6 having the absolute stereochemistry shown as a pale yellow oil, m/z=349 [M+H]+.

Method 7 Preparation of Aldehyde Compound 7

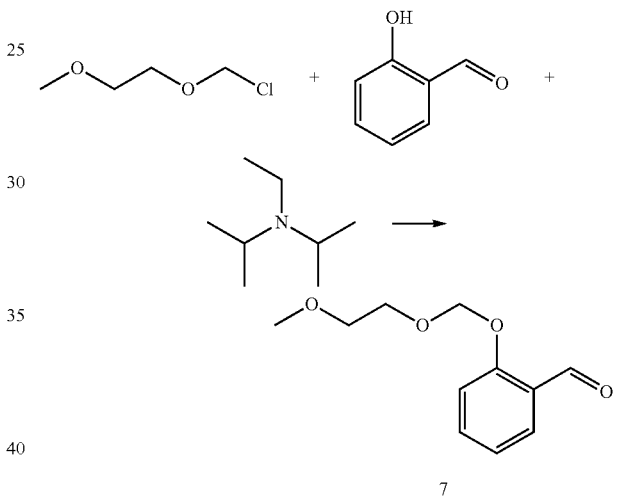

The aldehyde compound 7 was prepared according to literature procedure described in Breslow, R.; Schephartz, A. JACS, 1987, 109, 1814. Hinterman, L.; Masuo, R.; Suzuki, K. Org. Lett. 2008, 10, 21, 4859, incorporated by reference herein.

Method 8 Preparation of Compound 8

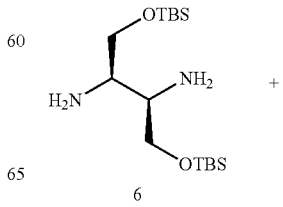

-continued

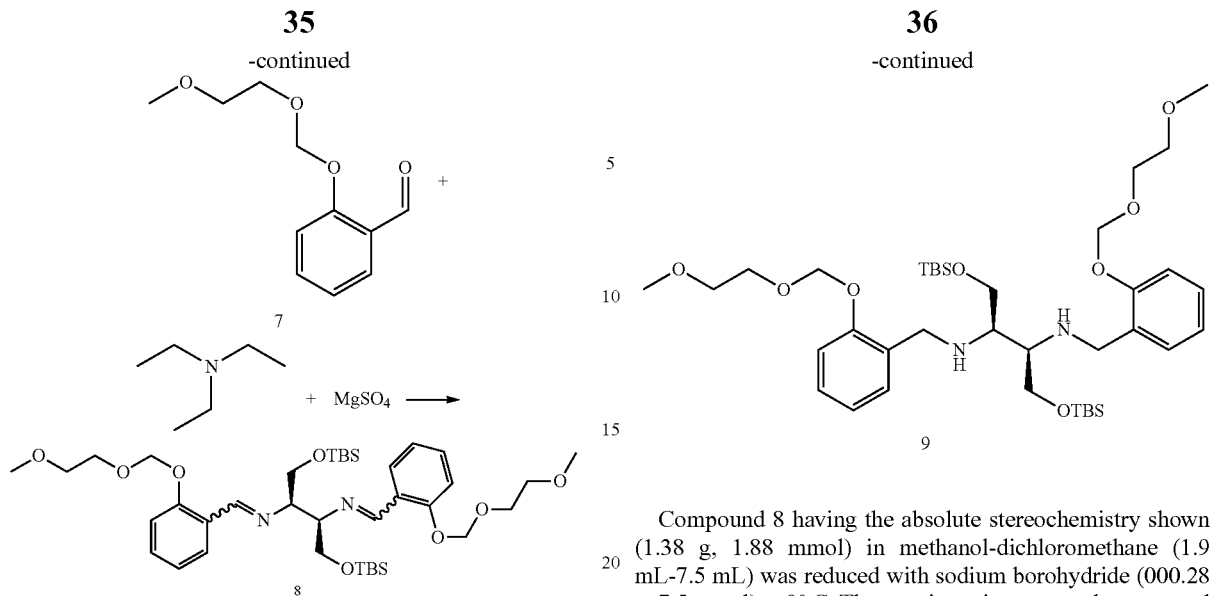

To a suspension of the diamine compound 6 having the absolute stereochemistry shown (1.3 g, 3.73 mmol) in dichloromethane (10 mL), triethylamine (0.94 g, 9.32 mmol) and MgSO$_4$ (1.80 g, 14.9 mmol) were added under stiffing conditions. After stirring for about 1.5 h at room temperature a solution of the aldehyde compound 7 (1.57 g, 7.46 mmol) in dichloromethane (5 mL) was added. The reaction mixture was allowed to stir overnight. The imine product being highly sensitive to hydrolysis care was taken to exclude water from the workup and chromatographic steps. The reaction mixture was filtered to remove solid materials and then concentrated under reduced pressure to provide a crude product. The crude product was triturated with diethyl ether, filtered, and concentrated under reduced pressure to provide a yellow oil that was dried in vacuo. The complete conversion to compound 8 having the absolute stereochemistry shown was confirmed by NMR spectroscopy. $^1$H NMR (CD$_2$Cl$_2$, 400 MHz) δ 0.06 (s, 6H), 0.11 (s, 6H), 0.93 (s, 18H), 3.36 (s, 6H), 3.54-3.58 (m, 4H), 3.65-3.70 (m, 2H), 3.75-3.80 (m, 2H), 3.81-3.84 (m, 4H), 4.07-4.13 (m, 2H), 5.32 (s, 4H), 7.03-7.09 9m, 2H), 7.20-7.25 (m, 2H), 7.37-7.43 (m, 2H), 8.01-8.07 (m, 2H) and 8.76 (s, 2H); $^{13}$C{$^1$H} NMR δ −5.49, 18.13, 25.69, 50.60, 66.83, 67.92, 71.59, 74.55, 93.70, 114.66, 121.65, 125.61, 127.42, 131.52, 156.77, and 157.86.

Method 9 Preparation of Diamine Compound 9

-continued

Compound 8 having the absolute stereochemistry shown (1.38 g, 1.88 mmol) in methanol-dichloromethane (1.9 mL-7.5 mL) was reduced with sodium borohydride (000.28 g, 7.5 mmol) at 0° C. The reaction mixture was then warmed to room temperature overnight. The reaction mixture was quenched by the addition of saturated aqueous potassium carbonate solution. The aqueous and organic layers were separated and the aqueous layer was extracted with dichloromethane (3×25 mL) and the combined organic layers were washed with saturated aqueous sodium bicarbonate solution, (2×25 mL), brine (2×25 mL) and dried over MgSO$_4$. The solution was filtered and concentrated under reduced pressure to provide the crude product as a pale yellow oil which was purified by flash chromatography (SiO$_2$, 40 gram column) using the following gradient program at 60 mL/min: 100% dichloromethane w/0.5% triethylamine for 3 column volumes, then ramp to 5% MeOH-Dichloromethane each w/0.5% triethylamine over 20 column volumes, finally holding at 5% MeOH-Dichloromethane each w/0.5% triethylamine for 5 column volumes. The column eluant was monitored at 285 nm and the fractions containing the purified material were pooled, concentrated under reduced pressure and then dried in vacuo to yield purified diamine compound 9 having the absolute stereochemistry shown as a colorless oil, m/z=738 [M+H]+.

Example 5

Preparation of Ligand XV

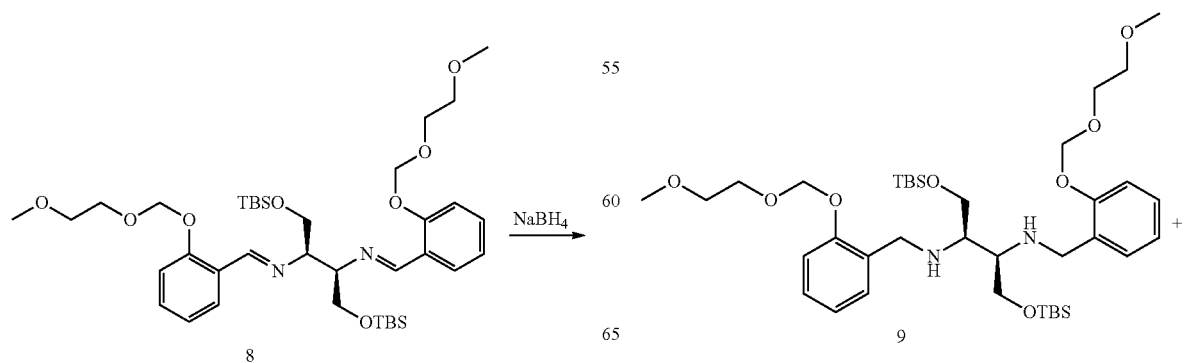

-continued

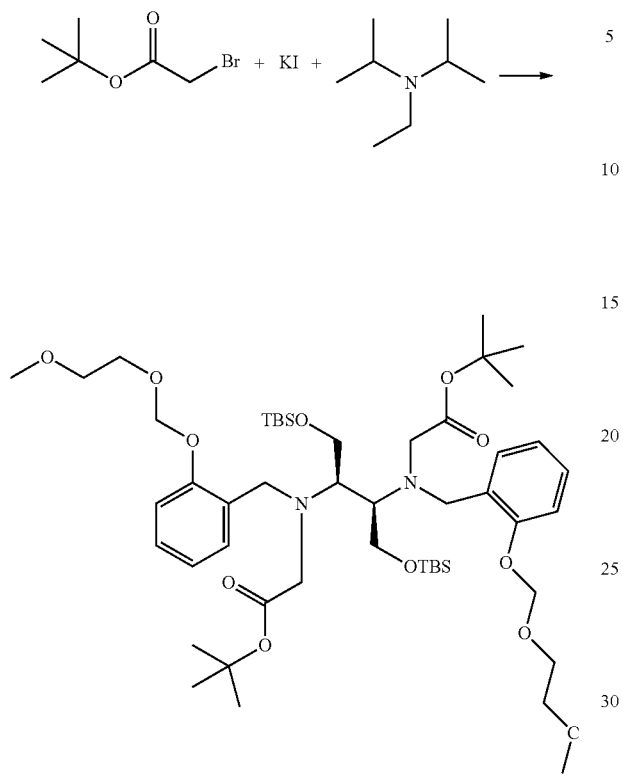

XV

Example 6

Preparation of FeHBED(OH')$_2$ VII

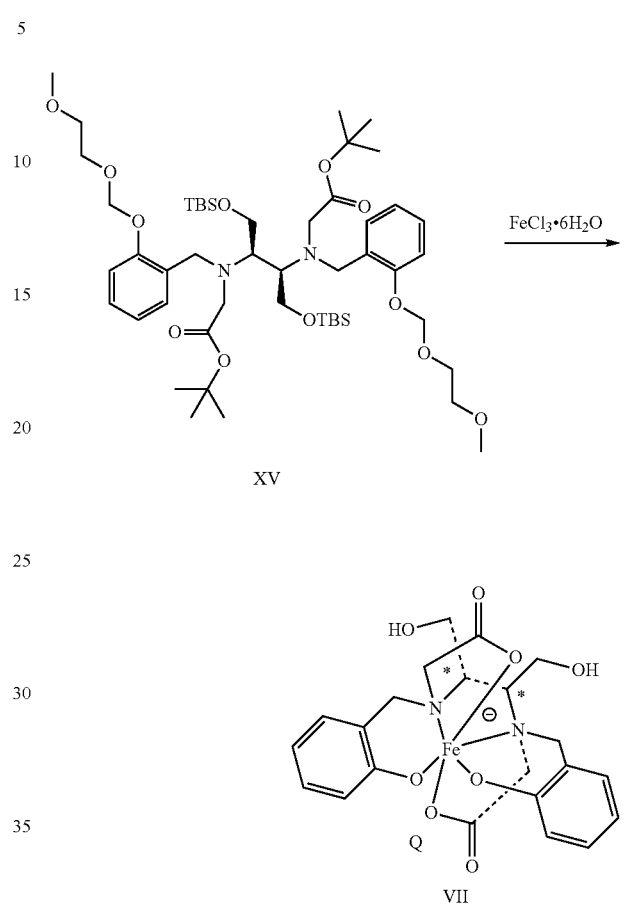

An aliquot of Hunig's base (0.20 g, 1.55 mmol) was added to a DMF (2.9 mL) solution of diamine compound 9 having the absolute stereochemistry shown (0.29 g, 0.39 mmol) and the entire mixture allowed to stir for 30 min. In a separate vial, potassium iodide (0.19 g, 1.16 mmol) was dissolved in DMF (1 mL) and combined with tert-butyl bromoacetate (0.16 g, 0.82 mmol). After stirring for 30 min the potassium iodide mixture was added to the reaction vessel that contained diamine compound 9 and Hunig's base. The stirring was continued stirring overnight at a temperature of about 80° C. An LC-MS was carried out that indicated that the reaction had proceeded to completion and contained small amount of impurities. The volatiles were removed under reduced pressure. The residue was dissolved in THF prior to being filtered in order to remove the precipitated salts. The crude product was then adsorbed onto SiO$_2$ and purified by flash chromatography (SiO$_2$, 12 gram column) using the following gradient program at 30 mL/min: 20% EtOAc-hexanes w/0.5% triethylamine for 3 column volumes, then ramp to 88% EtOAc-hexanes w/0.5% triethylamine over 20 column volumes, finally holding at 88% EtOAc-hexanes w/0.5% triethylamine for 5 column volumes. The column eluant was monitored at 277 nm and the purified material was pooled and concentrated under reduced pressure. Drying in vacuo provided the purified ligand XV having the absolute stereochemistry shown, as a colorless oil, m/z=966 [M+H]+.

To a solution of the ligand XV having the absolute stereochemistry shown (0.18 g, 0.18 mmol) in dioxane (1.22 mL) and water (1.22 mL) was added FeCl$_3$.6H$_2$O (5.7 mg, 0.17 mmol). The reaction mixture was treated 4M HCl in dioxane (1.22 mL) and stirred at room temperature overnight. At the end of the allotted time, the solution was heated to a temperature of about 75° C. in an oil bath for about 2 h and the completion of the reaction was confirmed by LC-MS analysis of a reaction aliquot, which has been neutralized in saturated aqueous sodium bicarbonate. The reaction mixture was then cooled to about 0° C. in an ice bath and quenched with aqueous sodium bicarbonate. This was followed by dilution in deionized water (10 mL) and addition of dichloromethane (10 mL). The aqueous and the organic layers were separated. The aqueous layer was washed with dichloromethane (3×25 mL) and the combined organic layers that were extracted with deionized water, (2×25 mL). The aqueous layers were combined and the volume reduced (50 torr, 40° C., 30 min). The concentrated red solution was then filtered through a 30,000 molecular weight cut-off filter and lyophilized to afford compound VII as a red solid having the same absolute stereochemistry at the centers marked with an asterisk (*) as shown in ligand XV, wherein the charge balancing counterion Q is sodium cation. LC-MS analysis of the product indicated compound VII was a mixture of two diastereomers in a 65:35 ratio, m/z=502 [M+H]+with trace amounts of free deprotected chelate.

Method 10 Preparation of Compound 10

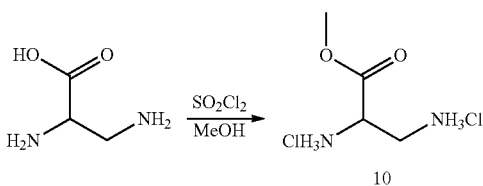

Thionyl chloride (31.7 g, 266.8 mmol) was added drop wise to a stirred suspension of 2,3-diaminopropionic acid monohydrochloride (5.0 g, 35.6 mmol) in methanol (75 mL) over a period of about 5 min. The reaction mixture was heated to about 80° C. for about 6 h. At the end of the stipulated time, the reaction mixture was cooled and the volatiles were removed under reduced pressure to obtain compound 10 (6.8 g, 100%) as an off-white solid. $^1$H NMR (MeOD): δ 4.51 (m, 1H), δ 3.96 (s, 3H), δ 3.53 (m, 2H).

Method 11 Preparation of Aldehyde Compound 11

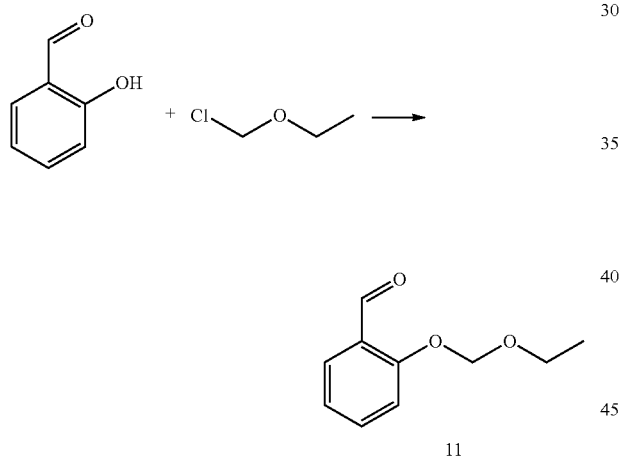

Diisopropylethylamine (8.64 g, 66.8 mmol) was added to a stirred solution of salicylaldehyde (5.83 g, 47.7 mmol) in dichloromethane (477 mL) maintained at a temperature of about 0° C. in an ice-bath. The reaction mixture was allowed to stand for about an hour. At the end of 1 hr, chloromethoxyethane (4.74 g, 50.1 mmol) was added drop wise over a period of 5 min and the pale yellow reaction mixture was warmed to ambient temperature and stirred for about 18 h. After the allotted time, the reaction mixture was diluted with a saturated aqueous ammonium chloride solution (100 mL) and the layers were separated. The aqueous layer was back extracted with dichloromethane (2×50 mL), while the organic layers were combined and dried over MgSO$_4$. The solution was filtered and the filtrate concentrated under reduced pressure to afford a yellow oil. This crude product was purified by column chromatography (SiO$_2$, hexanes to 1:9 ethyl acetate:hexanes) and compound 11 was obtained as a nearly colorless oil, m/z=181 [M+H]+.

Method 12 Preparation of Compound 12

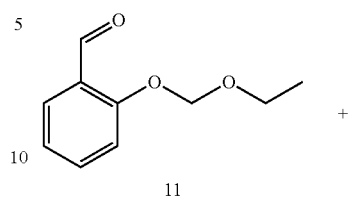

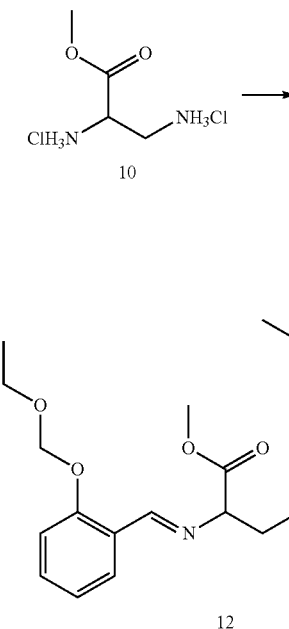

To a stirred solution of compound 10 (2.69 g, 14.1 mmol) in anhydrous methylene chloride (50 mL) was added triethylamine (6.41 g, 63.4 mmol). The reaction mixture stirred for about 45 min. About 6.78 g of MgSO$_4$ (56.3 mmol) was then added and the mixture was stirred for an additional 45 min. A solution of compound 11 (5.15 g, 28.6 mmol) in methylene chloride (5 mL) was then added over a period of 2 min and the colorless mixture was stirred for about 18 h at ambient temperature. At the end of 18 h the solids were filtered from the resulting yellow-orange reaction mixture and the filtrate concentrated to an oil. The oil was re-dissolved in methylene chloride and added to a stirred solution of diethyl ether (250 mL), resulting in the formation of a white precipitate. The solids were filtered and the filtrate concentrated to obtain compound 12 as a yellow-orange oil the structure of which was confirmed by NMR spectroscopy. $^1$H NMR (CD$_2$Cl$_2$): δ 8.72 (s, 1H), δ 8.70 (s, 1H), δ 7.98 (dd, J=7.0 Hz, J=7.0 Hz, 1H), δ 7.91 (dd, J=7.0 Hz, J=7.0 Hz, 1H), 7.38 (m, 2H), δ 7.15 (t, J=8.0 Hz, 2H), δ 7.02 (m, 2H), δ 5.23 (s, 4H), δ 4.43 (m, 1H), δ 4.32 (m, 1H), δ 3.91 (m, 1H), δ 3.79 (s, 3H), δ 3.68 (m, 4H), δ 1.19 (t, J=7.0 Hz, 1H).

Method 13 Preparation of Diamine Compound 13

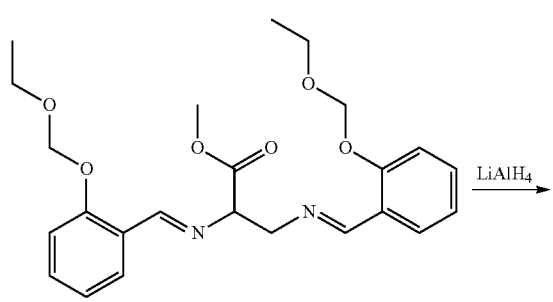

12

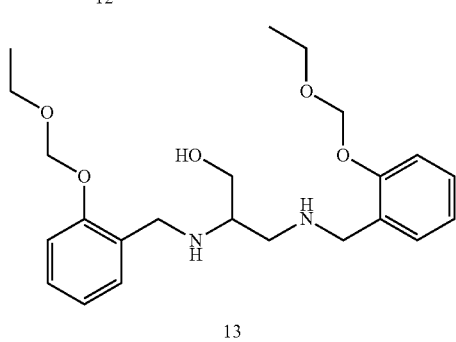

13

An anhydrous tetrahydrofuran (50 mL) solution of compound 12 (2.0 g, 4.52 mmol) was cooled to about 0° C. in an ice-bath with stirring while lithium aluminum hydride (0.69 g, 18.1 mmol) was added to the solution over a period of about 5 min to obtain a green-grey reaction mixture. The green-grey reaction mixture was warmed to ambient temperature and stirred for about 18 h. After the allotted time, deionized water (8-10 mL) was added drop wise over a period of 5 min and the reaction mixture was stirred for about 1.5 h. The resulting solids were filtered and the filtrate concentrated to afford the crude product as a yellow oil. The crude product was purified by column chromatography (SiO$_2$, 99% methylene chloride:1% triethylamine to 94% methylene chloride:5% methanol:1% triethylamine) to obtain the diamine compound 13 as a pale yellow oil, m/z=419 [M+H]+.

Method 14 Preparation of Diamine Compound 14

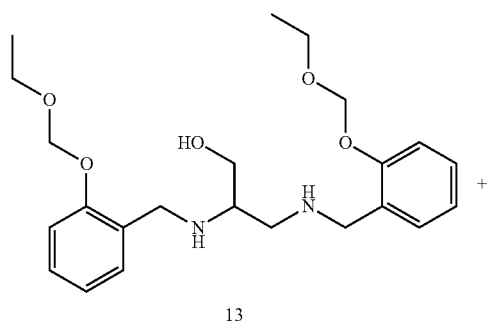

13

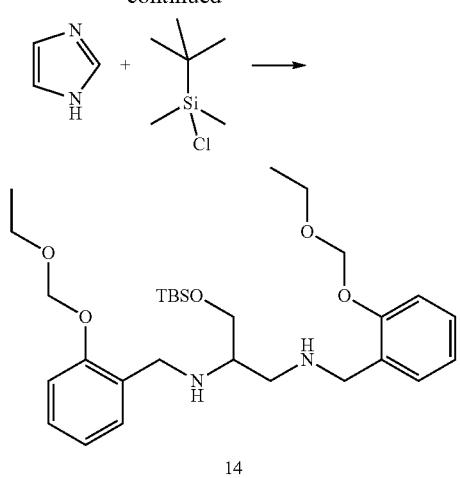

14

To a cooled (0° C.) stirred solution of diamine compound 13 (1.00 g, 2.39 mmol) in anhydrous dichloromethane (50 mL) was added imidazole (0.65 g, 9.56 mmol). About 0.38 g of tert-butyldimethylsilyl chloride (2.51 mmol) was added after 30 min. The resulting pale yellow reaction mixture was warmed to ambient temperature and the stirring was continued for about 18 h. At the end of 18 h, saturated aqueous potassium carbonate (50 mL) solution was added and the layers were separated. The aqueous layer was back extracted with dichloromethane (2×25 mL), and the organic layers were combined and then concentrated under reduced pressure to give yellow oil. The crude product was purified by column chromatography (silica, hexanes to 1:9 ethyl acetate:hexanes) to obtain the diamine compound 14 (1.08 g, 85%) as a nearly colorless oil, m/z=533 [M+H]+.

Method 15 Preparation of Aldehyde Compound 15

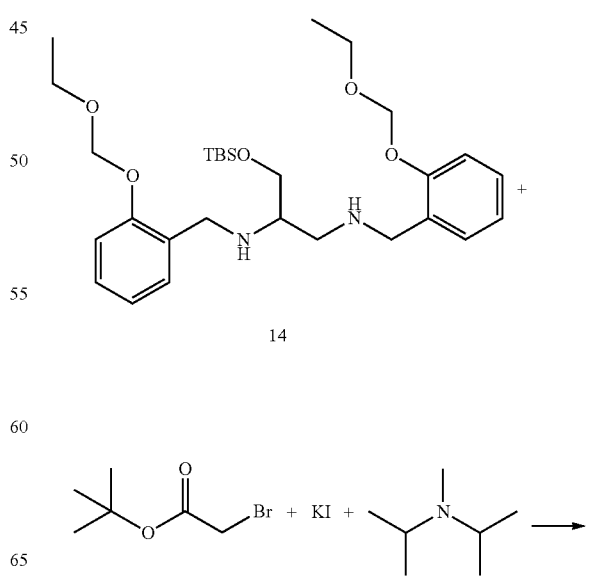

14

-continued

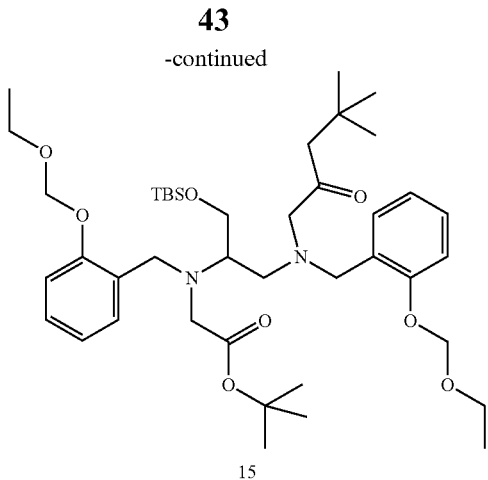

15

To a stirred solution of diamine compound 14 (1.08 g, 2.03 mmol) in N,N-dimethylformamide (20 mL) was added diisopropylethylamine (0.79 g, 6.08 mmol). The stirring was continued for about 45 min, followed by addition of a separate solution of a pre-stirred mixture of potassium iodide (1.35 g, 8.11 mmol) and tert-butylbromoacetate (0.83 g, 4.26 mmol) in N,N-dimethylformamide (5 mL) to the above solution. A pale yellow reaction mixture was obtained and the reaction mixture was heated to a temperature of about 80° C. for a period of about 18 h. The resulting reddish-brown solution was cooled to ambient temperature and concentrated under reduced pressure to form a dark crude oil. The dark crude oil was purified by column chromatography (SiO$_2$, hexanes to 1:9 ethyl acetate:hexanes) to obtain the diamine compound 15 (0.88 g, 57%) as a pale yellow oil. m/z=762 [M+H]+.

Example 7

Preparation of Ligand XVI

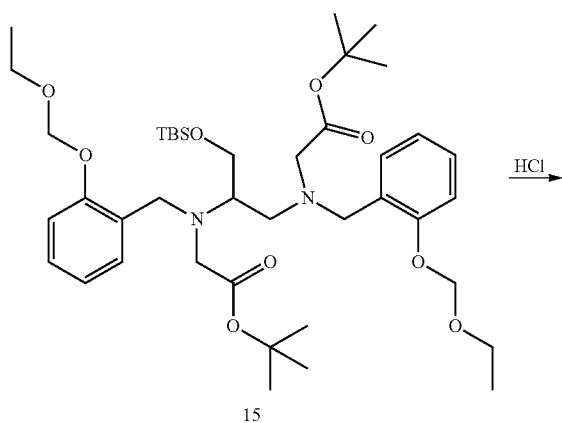

-continued

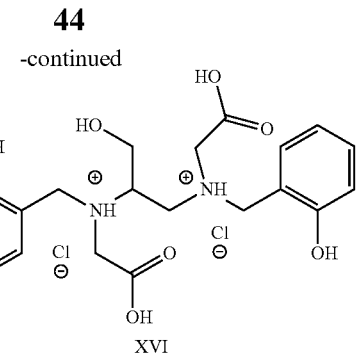

XVI

To a stirred solution of the diamine compound 15 (0.88 g, 1.15 mmol) in acetonitrile (1 mL) was added 1 M aqueous hydrochloric acid (2 mL) and the reaction heated to a temperature of about 50° C. for a period of about 18 h. At the end of the allotted time, the reaction mixture was neutralized with 5N sodium hydroxide (0.80 mL) to pH 7.1-7.3. The neutralized solution was concentrated under reduced pressure to obtain ligand XVI as an off white solid that was used without further purification, m/z=419 [M+H]+.

Example 8

Preparation of FeHBED(OH) VI

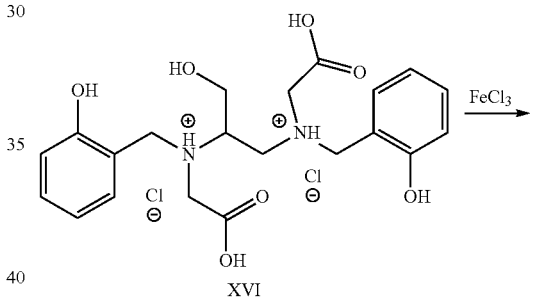

XVI

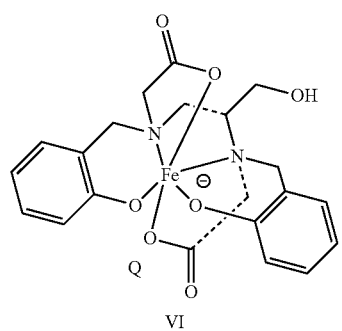

VI

The ligand XVI (488 mg, 1.15 mmol) was dissolved in MeOH (7 mL) to provide a clear colorless solution. An orange solution of FeCl$_3$ (132 mg, 81 mmol) dissolved in MeOH (3 mL) was added dropwise to the ligand solution to form a purple reaction mixture. The purple reaction mixture was stirred for about 10 min, followed by dropwise addition of an aliquot of NEt$^i$Pr$_2$ (300 µL, 1.7 mmol) over the course of 5 min resulting in the formation of a clear dark red solution with a pH of 6.5. The dark red solution was allowed to stir for about 12 h and then extracted with Et$_2$O (3×15 mL), and was combined with deionized water (5 mL) and passed through a Sephadex G10 plug (2 g). The solution was then eluted with deionized water (2×10 mL) followed by MeOH (2×10 mL) to afford a clear red solution. The clear red solution was lyophilized to provide the compound VI, wherein the charge balancing counterion Q is the protonated form of NEt$^i$Pr$_2$, as a red solid (269 mg, 56% yield). LC-MS 472 m/z [M+H]+. UV-Vis (DI) $\lambda_{max}$=492 nm.

Method 16 Preparation of Aldehyde Compound 16

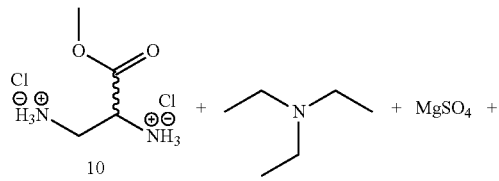

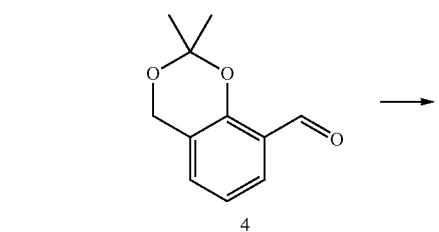

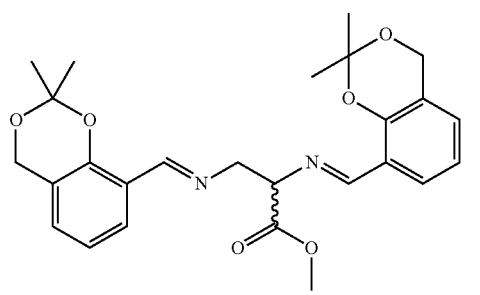

Triethylamine (2.38 g, 23.6 mmol) and MgSO$_4$ (2.52 g, 20.5 mmol) were added to a suspension of the diamine compound 10 (1.00 g, 5.23 mmol) in dichloromethane (15 mL). The reaction mixture was stirred for about 1.5 h at room temperature followed by addition of a dichloromethane (6 mL) solution of the aldehyde compound 4 (2.04 g, 10.4 mmol) and stirred overnight. As the imine product being highly sensitive to hydrolysis care was taken to exclude water from the workup and chromatographic steps. The reaction mixture was then filtered to remove solid materials and concentrated under reduced pressure to provide the compound 16 containing a small quantity of unreacted aldehyde as confirmed by NMR. $^1$H NMR (CD$_2$Cl$_2$, 400 MHz) δ 1.50 (s, 3H), 1.51 (s, 3H), 1.58 (s, 6H), 3.81 (s, 3H), 3.92-4.00 (m, 1H), 4.33-4.41 (m, 1H), 4.45-4.51 (m, 1H), 4.85 (s, 4H), 6.92-6.97 (m, 2H), 7.02-7.08 (m, 2H), 7.84-7.88 (m, 1H), 7.92-7.96 (m, 1H), 8.69 (s, 1H), and 8.71 (s, 1H); $^{13}$C{$^1$H} NMR δ 24.38, 24.43, 24.73, 24.78, 46.20, 52.00, 60.62, 63.41, 73.51, 100.04, 100.15, 119.99, 120.01, 123.62, 124.00, 125.57, 125.79, 127.12, 127.57, 130.90, 150.94, 151.21, 158.63, 159.72, 171.48, and 188.59.

Method 17 Preparation of Diamine Compound 17

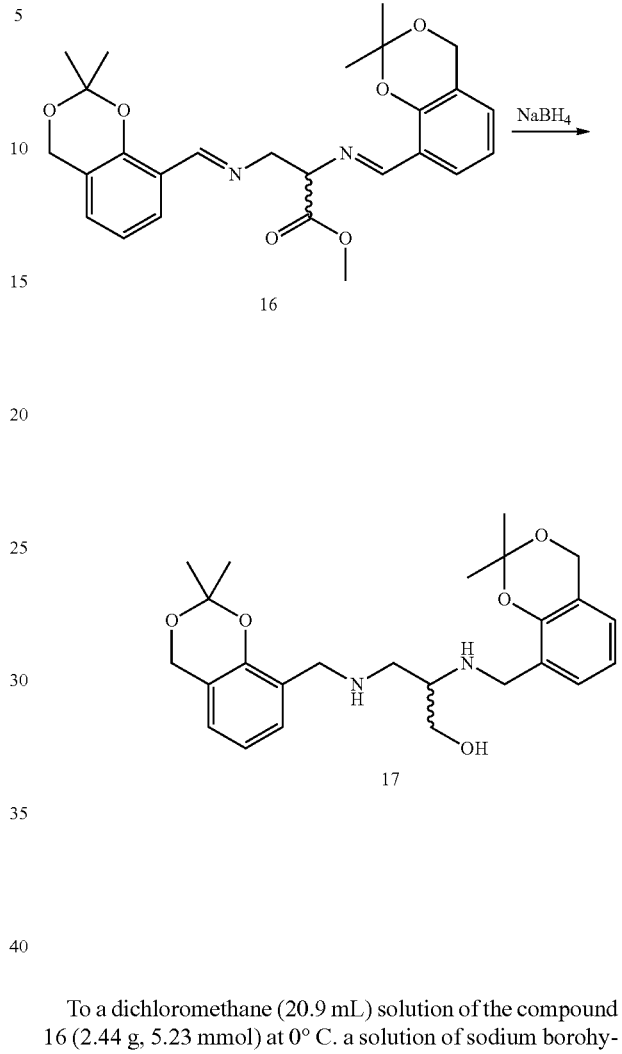

To a dichloromethane (20.9 mL) solution of the compound 16 (2.44 g, 5.23 mmol) at 0° C. a solution of sodium borohydride (1.19 g, 31.4 mmol) in methanol (5.23 mL) was added via an additional funnel. Stirring was continued overnight while the reaction mixture was allowed slowly attain room temperature. The reaction mixture was then quenched by the addition of a saturated aqueous potassium carbonate solution. The aqueous layer and the organic layers were separated. The aqueous layer was extracted with dichloromethane (3×25 mL) and the combined organic layers were washed with saturated aqueous sodium bicarbonate solution, (2×25 mL), brine (2×25 mL) and dried over MgSO$_4$. The solution was then filtered and concentrated under reduced pressure to provide the crude product as a pale yellow oil. The crude product was purified by flash chromatography (SiO$_2$, 40 gram column) using the following gradient program at 60 mL/min: 100% dichloromethane w/0.5% triethylamine for 3 column volumes, then ramp to 5% MeOH-Dichloromethane each w/0.5% triethylamine over 20 column volumes, finally holding at 5% MeOH-Dichloromethane each w/0.5% triethylamine for 5 column volumes. The column eluant was monitored at 285 nm and the fractions containing the purified material were pooled and concentrated under reduced pressure. The diamine compound 17 was obtained as a colorless oil that was dried under high vacuum, m/z=444 [M+H]+.

Example 9

Preparation of Ligand XVII

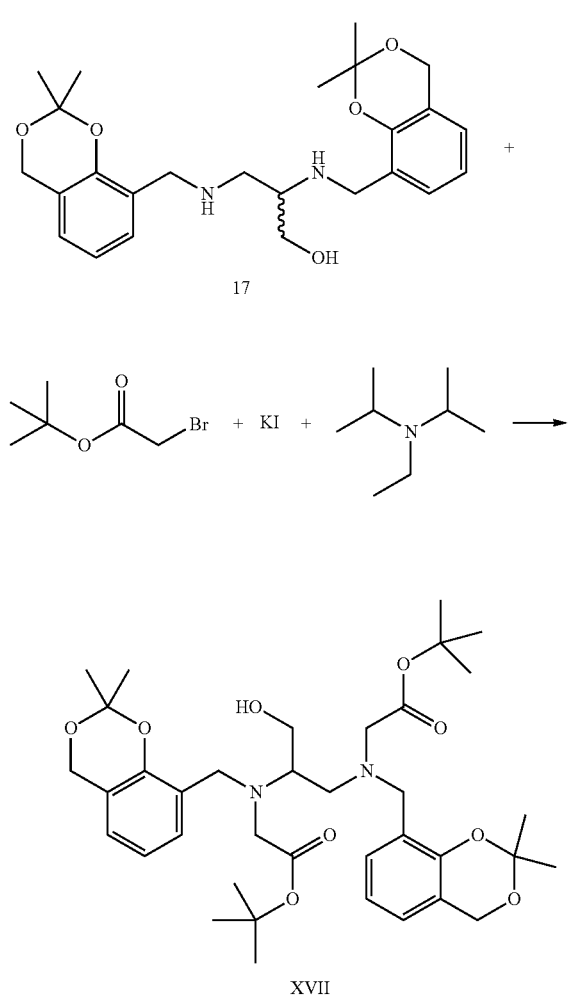

The diamine compound 17 was dissolved in DMF (7.5 mL) followed by addition of Hunig's base (0.49 g, 3.8 mmol) and the mixture was stirred for about 30 min. In a separate vial, tert-butylbromoacetate (0.39 g, 2.0 mmol) was added to a DMF (2 mL) solution of potassium iodide (0.47 g, 2.9 mmol) and the mixture was stirred for about 30 min. The potassium iodide mixture was then added to the vessel that contained diamine compound 17 and the reaction mixture was stirred overnight at a temperature of about 80° C. The reaction mixture was analyzed by LC-MS that indicated that the reaction had proceeded to completion and contained only a small impurity. The reaction mixture was concentrated under reduced pressure to remove the DMF, and the residue was dissolved in THF and filtered to remove the salts. The THF solution was then adsorbed onto $SiO_2$ and purified by column chromatography ($SiO_2$, 12 g column, 17.5% EtOAc-25% EtOAc:hexanes over 25 column volumes (CV) eluant was observed at 281 nm). The isolated product fractions were concentrated under reduced pressure and dried in vacuo to obtain ligand XVII as a colorless oil, LCMS m/z=672 [M+H]$^+$, 693 [M+Na]+.

Example 10

Preparation of Compound V

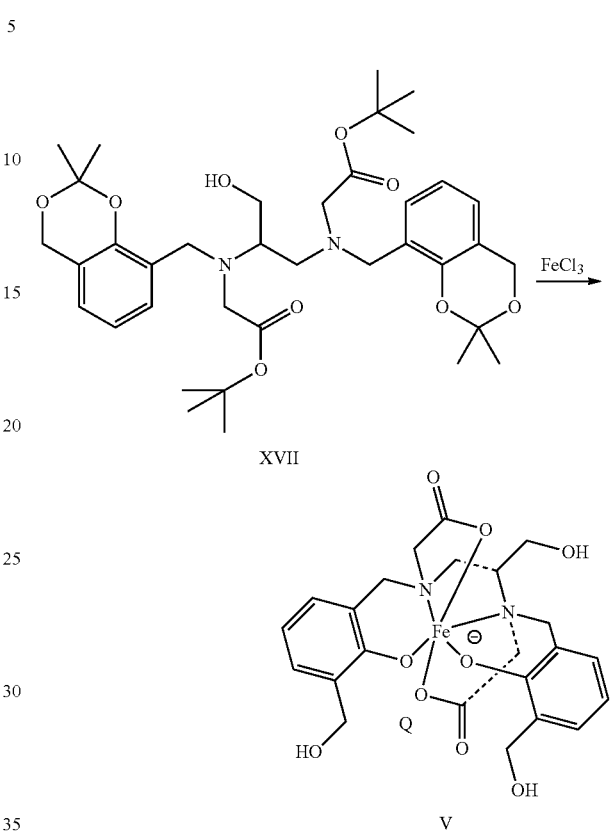

The ligand XVII was dissolved in acetonitrile (1.38 mL) and water (0.17 mL). The ligand solution was combined with $FeCl_3$ (3.6 mg, 22.6 mmol) and then concentrated HCl (12 M, 172 μL) before it was sealed and heated to a temperature of about 70° C. The progress of the reaction was monitored by LC-MS analysis of aliquots quenched in saturated aqueous sodium bicarbonate solution and appeared was completed at the end of about 4 h. The reaction mixture was then quenched by the addition of saturated aqueous sodium bicarbonate solution and concentrated to dryness. The isolated material was dissolved in a minimal amount of water and filtered through a 5 μm nylon filter. The crude product was purified by preparative HPLC on C18 functionalized silica gel (10×100 mm waters xTerra Prep C18 5 μm) using the following gradient program at 9 mL/min: 100% water for 0.5 minutes, then ramp to 10% MeCN-water containing 0.05% TFA over 14.5 minutes, finally holding at 10% MeCN-water containing 0.05% TFA for 3 minutes. The column eluant was monitored at 494 nm and the fractions containing the purified material were pooled and concentrated under reduced pressure. The purified material was dried under high vacuum to obtain the compound V wherein Q is a sodium cation as a red solid, m/z=532 [M+H]+, 554 [M+Na]+. UV-Vis (DI) $\lambda_{max}$=494 nm

Relaxivity Determinations

A stock solution having a concentration of 1 mM of the contrast enhancement agent was prepared in phosphate buffered saline (PBS) and the iron concentration was verified by elemental analysis. Separate 0.75 mM, 0.50 mM and 0.25 mM samples were prepared from the stock by dilution in PBS and the $T_1$ and $T_2$ relaxations times were recorded in triplicate for each using sample on a Bruker Minispec mq60 instrument (60 MHz, 40° C.). The relaxivities ($r_1$ and $r_2$) were obtained as the gradient of $1/T_x$ (x=1,2) plotted against Fe chelate concentration following linear least squares regression analysis.

Data for contrast enhancement agents having structures III, IV, V, VI, VII, and VII, and a non-hydroxylated control contrast enhancement agent. Data are gathered in Table V below and illustrate the surprising effect of hydroxylation on the relaxivities exhibited by the contrast enhancement agents provided by the present invention relative to the control sample.

TABLE V

Relaxivities Of Representative Contrast Enhancement Agents

| Chelate Structure | | No. Hydroxy Groups | $r_1 (mM^{-1} \cdot s^{-1})$ | $r_2 (mM^{-1} \cdot s^{-1})$ |
|---|---|---|---|---|
| Control | [structure] | 0 | 0.5 | 0.5 |
| III | [structure] | 2 | 0.9 | 1.0 |
| IV | [structure] | 2 | 0.8 | 1.0 |

TABLE V-continued

Relaxivities Of Representative Contrast Enhancement Agents

| Chelate Structure | No. Hydroxy Groups | $r_1(mM^{-1} \cdot s^{-1})$ | $r_2(mM^{-1} \cdot s^{-1})$ |
|---|---|---|---|
| V | 3 | 0.9 | 1.0 |
| VI | 1 | 1.1 | 1.5 |
| VII | 2 | 1.0 | 1.1 |
| VIII | 4 | — | — |

The foregoing examples are merely illustrative, serving to illustrate only some of the features of the invention. The appended claims are intended to claim the invention as broadly as it has been conceived and the examples herein presented are illustrative of selected embodiments from a manifold of all possible embodiments. Accordingly, it is the Applicants' intention that the appended claims are not to be limited by the choice of examples utilized to illustrate features of the present invention. As used in the claims, the word "comprises" and its grammatical variants logically also subtend and include phrases of varying and differing extent such as for example, but not limited thereto, "consisting essentially of" and "consisting of:" Where necessary, ranges have been supplied; those ranges are inclusive of all sub-ranges there between. It is to be expected that variations in these ranges will suggest themselves to a practitioner having ordinary skill in the art and where not already dedicated to the public, those variations should where possible be construed to be covered by the appended claims. It is also anticipated that advances in science and technology will make equivalents and substitutions possible that are not now contemplated by reason of the imprecision of language and these variations should also be construed where possible to be covered by the appended claims.

What is claimed is:

1. A contrast enhancement agent comprising an iron chelate having structure I

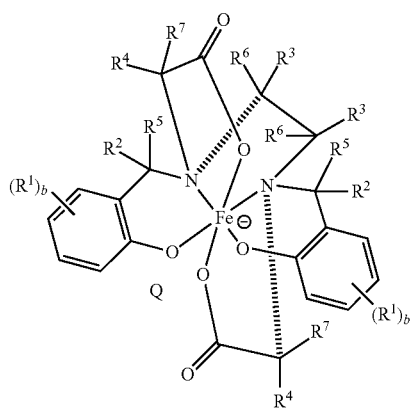

(I)

wherein $R^1$ is independently at each occurrence a hydroxy group, a $C_1$-$C_3$ hydroxyalkyl group, or a $C_1$-$C_3$ alkyl group, and b is 0-4; $R^2$-$R^7$ are independently at each occurrence hydrogen, a $C_1$-$C_3$ hydroxyalkyl group, or a $C_1$-$C_3$ alkyl group, with the proviso that at least one of $R^1$-$R^7$ is a hydroxy group or a $C_1$-$C_3$ hydroxyalkyl group and that when one of $R^4$ and $R^7$ is a $C_1$-$C_3$ hydroxyalkyl group at least one of $R^1$, $R^2$, $R^3$, $R^5$, or $R^6$ is also a $C_1$-$C_3$ hydroxyalkyl group; and wherein Q is a charge balancing counterion.

2. The contrast enhancement agent according to claim 1 which is a racemate, a single enantiomer, an enantiomerically enriched composition, or a mixture of diastereomers.

3. A contrast enhancement agent having structure II

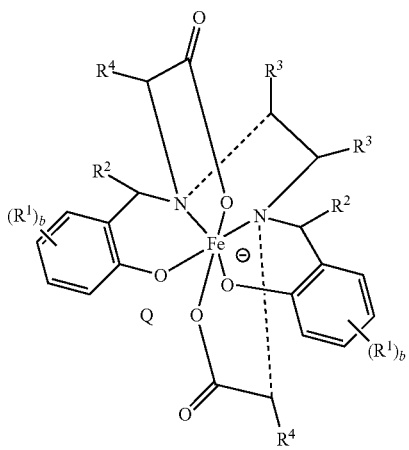

(II)

wherein $R^1$ is independently at each occurrence a hydroxy group, a $C_1$-$C_3$ hydroxyalkyl group, or a $C_1$-$C_3$ alkyl group, and b is 0-4; $R^2$-$R^4$ are hydrogen, a $C_1$-$C_3$ hydroxyalkyl group, or a $C_1$-$C_3$ alkyl group, with the proviso that at least one of $R^1$-$R^4$ is a hydroxy group or $C_1$-$C_3$ hydroxyalkyl group and that when $R^4$ is a $C_1$-$C_3$ hydroxyalkyl group at least one of $R^1$, $R^2$, or $R^3$ is also a $C_1$-$C_3$ hydroxyalkyl group; and wherein Q is a charge balancing counterion.

4. The contrast enhancement agent according to claim 3 which is a racemate, a single enantiomer, an enantiomerically enriched composition, or a mixture of diastereomers.

5. The contrast enhancement agent according to claim 2, having structure III

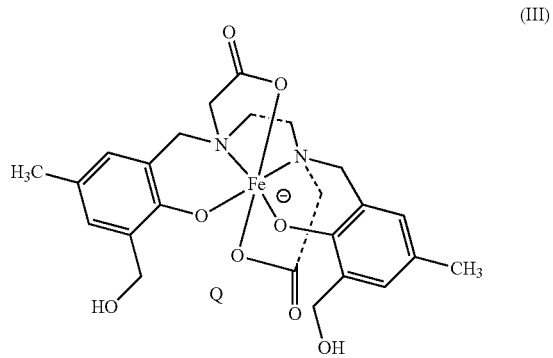

(III)

wherein Q is a charge balancing counterion.

6. The contrast enhancement agent according to claim 2, having structure IV

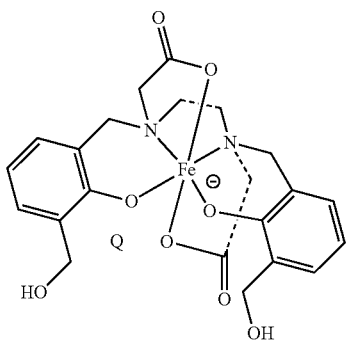

(IV)

wherein Q is a charge balancing counterion.

7. The contrast enhancement agent according to claim 2, having structure V

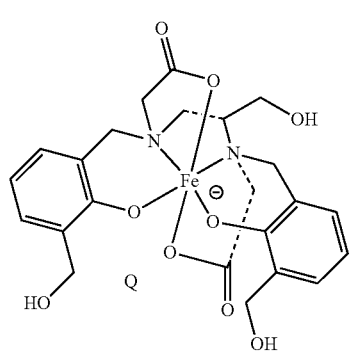

(V)

wherein Q is a charge balancing counterion.

8. The contrast enhancement agent according to claim 2, having structure VI

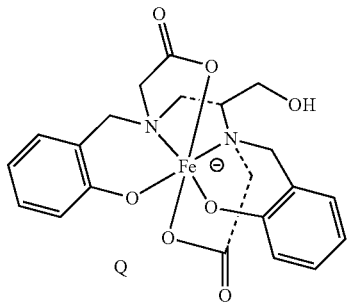

(VI)

wherein Q is a charge balancing counterion.

9. The contrast enhancement agent according to claim 2, having structure VII

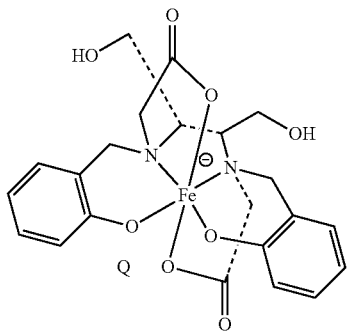

(VII)

wherein Q is a charge balancing counterion.

10. The contrast enhancement agent according to claim 2, having structure VIII

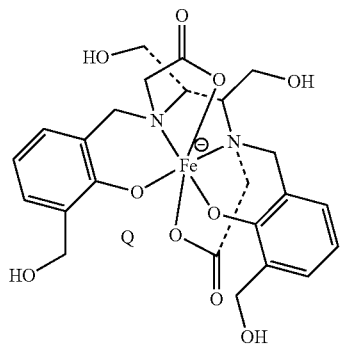

(VIII)

wherein Q is a charge balancing counterion.

11. A metal chelating ligand having idealized structure IX

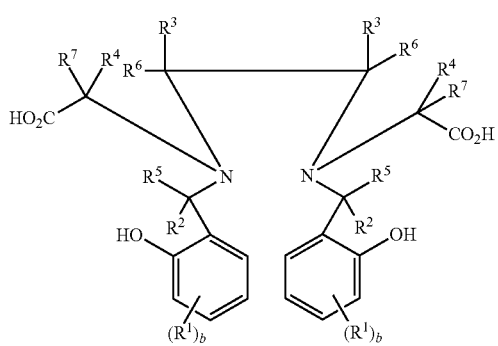

(IX)

wherein $R^1$ is independently at each occurrence a hydroxy group, a $C_1$-$C_3$ hydroxyalkyl group, or a $C_1$-$C_3$ alkyl group, and b is 0-4; $R^2$-$R^7$ are independently at each occurrence hydrogen, a $C_1$-$C_3$ hydroxyalkyl group, or a $C_1$-$C_3$ alkyl group, with the proviso that at least one of $R^1$-$R^7$ is a hydroxy group or a $C_1$-$C_3$ hydroxyalkyl group and that when one of $R^4$ and $R^7$ is a $C_1$-$C_3$ hydroxyalkyl group at least one of $R^1$, $R^2$, $R^3$, $R^5$, or $R^6$ is also a $C_1$-$C_3$ hydroxyalkyl group.

12. A metal chelating ligand having idealized structure X

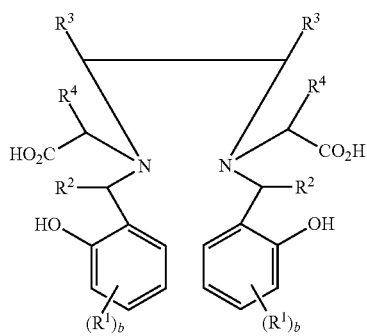

(X)

wherein $R^1$ is independently at each occurrence a hydroxy group, a $C_1$-$C_3$ hydroxyalkyl group, or a $C_1$-$C_3$ alkyl group, and b is 0-4; $R^2$-$R^4$ are hydrogen, a $C_1$-$C_3$ hydroxyalkyl group, or a $C_1$-$C_3$ alkyl group, with the proviso that at least one of $R^1$-$R^4$ is a hydroxy group or $C_1$-$C_3$ hydroxyalkyl group and that when $R^4$ is a $C_1$-$C_3$ hydroxyalkyl group at least one of $R^1$, $R^2$, or $R^3$ is also a $C_1$-$C_3$ hydroxyalkyl group.

13. The metal chelating ligand according to claim 11, having idealized structure XI

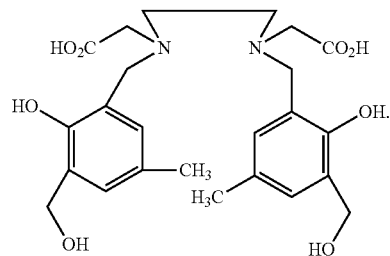

(XI)

14. The metal chelating ligand according to claim 11, having idealized structure XII

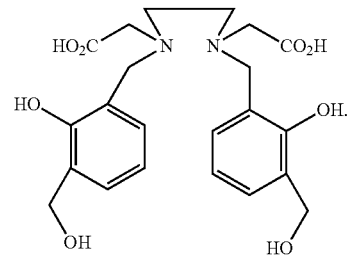

(XII)

15. The metal chelating ligand according to claim 11, having idealized structure XIII

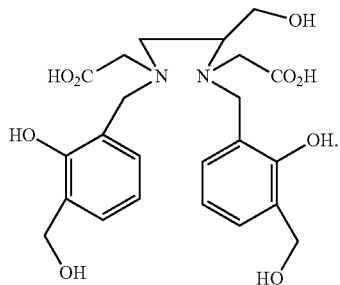
(XIII)

16. The metal chelating ligand according to claim 11, having idealized structure XIV

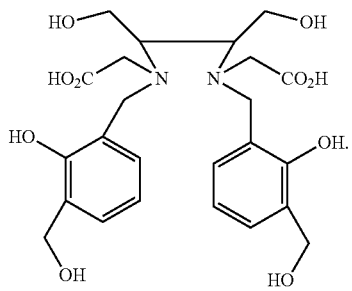
(XIV)

17. A medical formulation comprising a contrast enhancement agent having structure I

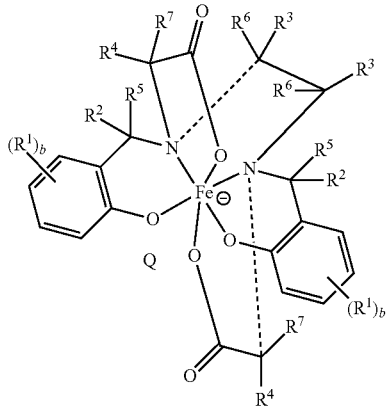
(I)

wherein $R^1$ is independently at each occurrence a hydroxy group, a $C_1$-$C_3$ hydroxyalkyl group, or a $C_1$-$C_3$ alkyl group, and b is 0-4; $R^2$-$R^7$ are independently at each occurrence hydrogen, a $C_1$-$C_3$ hydroxyalkyl group, or a $C_1$-$C_3$ alkyl group, with the proviso that at least one of $R^1$-$R^7$ is a hydroxy group or a $C_1$-$C_3$ hydroxyalkyl group and that when one of $R^4$ and $R^7$ is a $C_1$-$C_3$ hydroxyalkyl group at least one of $R^1$, $R^2$, $R^3$, $R^5$, or $R^6$ is also a $C_1$-$C_3$ hydroxyalkyl group; and wherein Q is a charge balancing counterion.

18. A medical formulation comprising a contrast enhancement agent having structure II

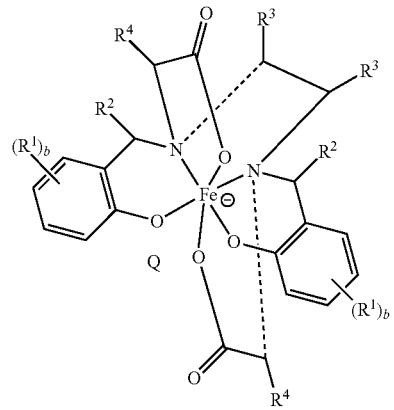
(II)

wherein $R^1$ is independently at each occurrence a hydroxy group, a $C_1$-$C_3$ hydroxyalkyl group, or a $C_1$-$C_3$ alkyl group, and b is 0-4; $R^2$-$R^4$ are hydrogen, a $C_1$-$C_3$ hydroxyalkyl group, or a $C_1$-$C_3$ alkyl group, with the proviso that at least one of $R^1$-$R^4$ is a hydroxy group or $C_1$-$C_3$ hydroxyalkyl group and that when $R^4$ is a $C_1$-$C_3$ hydroxyalkyl group at least one of $R^1$, $R^2$, or $R^3$ is also a $C_1$-$C_3$ hydroxyalkyl group; and wherein Q is a charge balancing counterion.

19. The medical formulation according to claim 17, having structure III

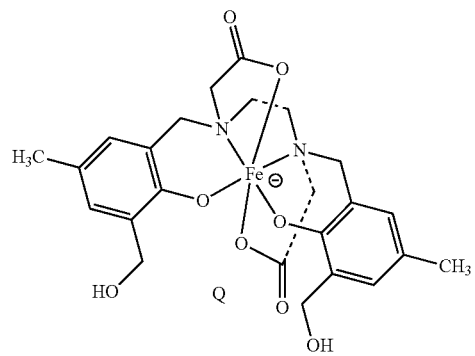
(III)

wherein Q is a charge balancing counterion.

20. The medical formulation according to claim 17, having structure IV

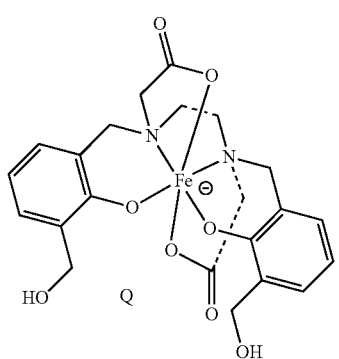
(IV)

wherein Q is a charge balancing counterion.

21. The medical formulation according to claim 17, having structure V

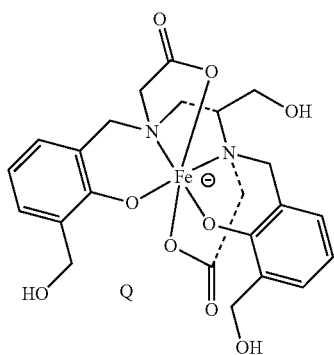

(V)

wherein Q is a charge balancing counterion.

22. The medical formulation according to claim 17, having structure VI

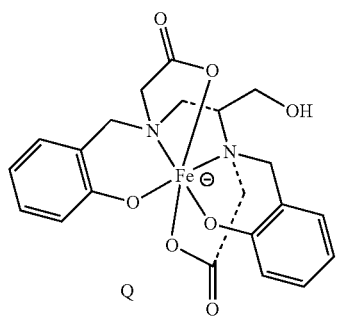

(VI)

wherein Q is a charge balancing counterion.

23. The medical formulation according to claim 17, having structure VII

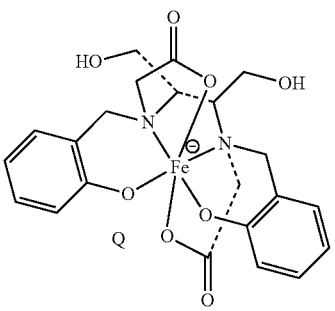

(VII)

wherein Q is a charge balancing counterion.

24. The medical formulation according to claim 17, having structure VIII

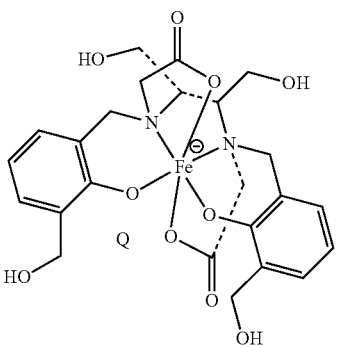

(VIII)

wherein Q is a charge balancing counterion.

* * * * *